(12) United States Patent
Erickson et al.

(10) Patent No.: US 9,610,259 B2
(45) Date of Patent: Apr. 4, 2017

(54) COMPOSITIONS AND METHODS FOR TREATING AN AUTISM SPECTRUM DISORDER

(71) Applicant: Children's Hospital Medical Center, Cincinnati, OH (US)

(72) Inventors: Craig Andrew Erickson, Wyoming, OH (US); Logan Kristen Wink, Cincinnati, OH (US); Tori Lynn Schaefer, Cincinnati, OH (US)

(73) Assignee: Children's Hospital Medical Center, Cinncinnati, OH (US)

(*) Notice: Subject to any disclaimer, the term of this patent is extended or adjusted under 35 U.S.C. 154(b) by 0 days.

(21) Appl. No.: 14/596,555

(22) Filed: Jan. 14, 2015

(65) Prior Publication Data
US 2015/0196501 A1    Jul. 16, 2015

Related U.S. Application Data

(60) Provisional application No. 61/926,991, filed on Jan. 14, 2014, provisional application No. 62/059,306, filed on Oct. 3, 2014.

(51) Int. Cl.
*A61K 31/135* (2006.01)
*A61K 45/06* (2006.01)
*A61K 9/00* (2006.01)

(52) U.S. Cl.
CPC .......... *A61K 31/135* (2013.01); *A61K 9/0043* (2013.01); *A61K 45/06* (2013.01)

(58) Field of Classification Search
CPC .................................................... A61K 31/135
See application file for complete search history.

(56) References Cited

U.S. PATENT DOCUMENTS

| | | | |
|---|---|---|---|
| 4,994,467 A | 2/1991 | Zimmerman | |
| 2009/0048348 A1 | 2/2009 | Chez | |
| 2014/0005173 A1* | 1/2014 | Conour | A61K 31/4406 514/211.13 |

FOREIGN PATENT DOCUMENTS

| | | |
|---|---|---|
| EP | 1567145 B1 | 8/2005 |
| WO | WO 2004/045601 | 6/2004 |
| WO | WO 2007/111880 | 10/2007 |
| WO | WO 2012/123819 | 9/2012 |
| WO | WO 2014/143646 | 9/2014 |

OTHER PUBLICATIONS

Aan Het Rot M, et al., "Ketamine for depression: where do we go from here?", Biol Psychiatry. Oct. 1, 2012; 72(7):537-547.
American Psychiatric Association. *Autism Spectrum Disorder; Diagnostic and Statistical Manual of Mental Disorders*, Fifth Edition. Arlington, VA: American Psychiatric Association; 2013, 2pgs.
Armstrong, T., et al., "Eye tracking of attention in the affective disorders: a meta-analytic review and synthesis", Clin Psychol Rev, 2012. 32(8): p. 704-23.
Aylward EH, et al., "Effects of age on brain volume and head circumference in autism", Neurology. Jul. 23, 2002; 59(2):175-183.
Bailey AR, et al., "Peripheral biomarkers in Autism: secreted amyloid precursor protein-alpha as a probably key player in early diagnosis", International journal of clinical and experimental medicine, 2008; 1(4):338-344.
Bailey DB, Jr., et al., "Autistic behavior, FMR1 protein, and developmental trajectories in young males with fragile X syndrome", J Autism Dev Disord., Apr. 2001;.31(2):165-174.
Barger SW, et al., "Microglial activation by Alzheimer amyloid precursor protein and modulation by apolipoprotein E", Nature. Aug. 28, 1997; 388(6645):878-881.
Berman RM, et al., "Antidepressant effects of ketamine in depressed patients", Biol Psychiatry, Feb. 15, 2000; 47(4):351-354.
Brentani, H., et al., "Autism spectrum disorders: an overview on diagnosis and treatment", Revista Brasileira de Psiquiatria, vol. 35, No. Suppl. 1, 2013, pp. S62-S72, XP002738648.
Bushell T, et al., "Pharmacological characterization of a non-inactivating outward current observed in mouse cerebellar Purkinje neurons", Br J Pharmacol., Feb. 2002;.135(3):705-712.
Carr, DB, et al., "Safety and efficacy of intranasal ketamine for the treatment of breakthrough pain in patients with chronic pain: a randomized, double-blind, placebo-controlled, crossover study", Pain. Mar. 2004; 108(1-2):17-27.
Chadman KK., "Fluoxetine but not risperidone increases sociability in the BTBR mouse model of autism", Pharmacol Biochem Behav, Jan. 2011; 97(3):586-594.
Chen Ly, et al., "Cystitis associated with chronic ketamine abuse", Psychiatry Clin Neurosci., Aug. 2009; 63(4):591.
Christensen, et al., "Safety and efficacy of intranasal ketamine for acute postoperative pain", Acute Pain, Elesevier, vol. 9, No. 4, Nov. 8, 2007, pp. 183-192, XP022364900.
Cook EH, Jr., "Genetics of autism", Child Adolesc Psychiatr Clin N Am, Apr. 2001;.10(2):333-350.
Courchesne E, et al., "Brain overgrowth in autism during a critical time in development: implications for frontal pyramidal neuron and interneuron development and connectivity", Int J Dev Neurosci., Apr.-May 2005; 23(2-3):153-170.
Courchesne E, et al., "Evidence of brain overgrowth in the first year of life in autism", JAMA, Jul. 16, 2003; 290(3):337-344.
Courchesne E, et al., "Unusual brain growth patterns in early life in patients with autistic disorder: an MRI study", Neurology, Jul. 24, 2001; 57(2):245-254.
Davidovitch M, et al., "Head circumference measurements in children with autism", J Child Neurol., Sep. 1996; 11(5):389-393.
Doble A, "The pharmacology and mechanism of action of riluzole", Neurology, Dec. 1996; 47(6 Suppl 4):S233-241.
Erickson CA, et al., "Acamprosate on Amyloid Precursor Protein in Youth with Idiopathic and Fragile X Syndrome-Associated Autism Spectrum Disorder", Paper presented at: American Academy of Child and Adolescent Psychiatry Annual Meeting 2013; Orlando, Florida.

(Continued)

*Primary Examiner* — Zohreh Fay
(74) *Attorney, Agent, or Firm* — Frost Brown Todd LLC

(57) ABSTRACT

Disclosed are compositions and methods for the treatment of a subject having an autism spectrum disorder. The disclosed compositions may contain racemic ketamine or S-ketamine. The disclosed methods of administering the compositions include intranasal administration to a subject having an autism spectrum disorder.

14 Claims, 4 Drawing Sheets

(56) References Cited

OTHER PUBLICATIONS

Erickson CA, et al., "A retrospective study of memantine in children and adolescents with pervasive developmental disorders", Psychopharmacology, Mar. 2007; 191 (1): 141-147.

Erickson CA, et al., "Eye Tracking Utilizing Age Matched Social Scenes and Geometric Shapes", May 2014. Conference Paper. Conference: 2014 International Meeting for Autism Research Abstract Only.

Erickson CA, et al., "Open-Label Memantine in Fragile X Syndrome", J Autism Dev Disord., Jul. 16, 2009.

Erickson CA, et al., "Open-label riluzole in fragile X syndrome", Brain Res., Mar. 22, 2011; 1380:264-270.

Erickson, CA, et al., "Glutamatergic function in autism", In: Heresco-Levy U, ed., Glutamate in Neuropsychiatric Disorders., Trivandrum, Kerala, India: Research Signpost; 2008.

Falck-Ytter, T., et al., "Eye tracking in early autism research", J Neurodev Disord, 2013. 5(1): p. 28.

Fumagalli E, et al., "Riluzole enhances the activity of glutamate transporters GLAST, GLT1 and EAAC1", Eur J Pharmacol., Jan. 14, 2008; 578(2-3):171176.

Gaietto K, et al., "Eye Tracking Utilizing Age Matched Social Scenes and Geometric Shapes", May 2014. Conference Paper. Conference: 2014 International Meeting for Autism Research Abstract Only.

Green SM, et al., "Clinical practice guideline for emergency department ketamine dissociative sedation in children", Ann Emerg Med., Nov. 2004; 44(5):460-471.

Green SM, et al., "Clinical practice guideline for emergency department ketamine dissociative sedation: 2011 update", Ann Emerg Med., May 2011; 57(5):449-461.

Green Sm, et al., "Inadvertent ketamine overdose in children: clinical manifestations and outcome", Ann Emerg Med., Oct. 1999; 34(4 Pt 1):492-497.

Green SM, et al., "Ketamine sedation in mentally disabled adults", Academic emergency medicine, Official Journal of the Society for Academic Emergency Medicine. Jan. 1999; 6(1):86-87.

Green SM, et al., "Predictors of airway and respiratory adverse events with ketamine sedation in the emergency department: an individual-patient data meta-analysis of 8,282 children", Ann Emerg Med., Aug. 2009; 54(2):158-168 e151-154.

Green SM, et al., "Predictors of emesis and recovery agitation with emergency department ketamine sedation: an individual-patient data meta-analysis of 8,282 children", Ann Emerg Med., Aug. 2009; 54(2):171-180 e171-174.

Greig NH, et al., "Selective butyrylcholinesterase inhibition elevates brain acetylcholine, augments learning and lowers Alzheimer beta-amyloid peptide in rodent", Proc Natl Acad Sci U S A,. Nov. 22, 2005; 102(47):1721317218.

Hatton DD, et al., "Autistic behavior in children with fragile X syndrome: prevalence, stability, and the impact of FMRP", Am J Med Genet A., Sep. 1, 2006; 140A(17):18041813.

Hazlett HC, et al., "Early brain overgrowth in autism associated with an increase in cortical surface area before age 2 years", Arch Gen Psychiatry, May 2011; 68(5):467-476.

He, Y., et al. "Neuroprotective agent riluzole potentiates postsynaptic GABA(A) receptor function", Neuropharmacology, Feb. 2002;42(2):199-209.

Huge, V., et al., "Effects of low-dose intranasal (S)-ketamine in patients with neuropathic pain", European Journal of Pain, Saunders, London, GB, vol. 14, No. 4, Apr. 1, 2010, pp. 387-394, XP026985780.

Hurko O., et al, "Novel drug development for amyotrophic lateral sclerosis", J Neurol Sci. Nov. 1, 2000; 180(1-2):21-28.

Ibrahim L, et al., "Rapid decrease in depressive symptoms with an N-methyl-d-aspartate antagonist in ECT-resistant major depression", Prog Neuropsychopharmacol Biol Psychiatry, Jun. 1, 2011; 35(4):1155-1159.

Jolly-Tornetta C, et al., "Regulation of amyloid precursor protein secretion by glutamate receptors in human Ntera 2 neurons", J Biol Chem, May 29, 1998; 273(22):14015-14021.

Julious, S. "Sample size of 12 per group rule of thumb for a pilot study", Pharmaceutical Statistics, 2005; 4:287-291.

Kalk N, et al., "The Clinical Pharmacology of Acamprosate", Br J Clin Pharmacol., 2012.

Kavalali Et, et al., "Spontaneous neurotransmission: an independent pathway for neuronal signaling?", Physiology, (Bethesda) Feb. 2011; 26(1):45-53.

Kim SH, et al., "Aberrant early-phase ERK inactivation impedes neuronal function in fragile X syndrome", Proc Nail Acad Sci USA, Mar. 18, 2008; 105(11):4429-4434.

King BH, et al., "Double-blind, placebo-controlled study of amantadine hydrochloride in the treatment of children with autistic disorder", J Am Acad Child Adolesc Psychiatry, Jun. 2001; 40(6):658-665.

Krystal JH, et al., "Rapid-acting glutamatergic antidepressants: the path to ketamine and beyond", Biol Psychiatry, Jun. 15, 2013; 73(12):1133-1141.

Lahiri DK, et al., "A critical analysis of new molecular targets and strategies for drug developments in Alzheimer's disease", Current drug targets, Feb. 2003; 4(2):97-112.

Lahiri DK, et al., "Autism as early neurodevelopmental disorder: evidence for an sAPPalpha-mediated anabolic pathway", Frontiers in cellular neuroscience. 2013; 7:94.

Lahiri DK, et al., "Tacrine alters the secretion of the beta-amyloid precursor protein in cell lines", J Neurosci Res. Apr. 15, 1994; 37(6):777-787.

Lahiri DK, et al., The secretion of amyloid beta-peptides is inhibited in the tacrine-treated human neuroblastoma cells. Brain Res Mol Brain Res. Nov. 20, 1998;62(2): 131-140.

Lahiri, DK, et al., "Developmental expression of the beta-amyloid precursor protein and heat-shock protein 70 in the cerebral hemisphere region of the rat brain", Ann N Y Acad Sci. Jun. 2002; 965:324-333.

Levitt P, et al., "The genetic and neurobiologic compass points toward common signaling dysfunctions in autism spectrum disorders", J Clin Invest., Apr. 2009; 119(4):747-754.

Malinovsky JM, et al., "Ketamine and norketamine plasma concentrations after i.v., nasal and rectal administration in children", Br J Anaesth., Aug. 1996; 77(2):203207.

Mattson MP, et al., "Signaling events regulating the neurodevelopmental triad. Glutamate and secreted forms of beta-amyloid precursor protein as examples", Perspectives on developmental neurobiology, 1998; 5(4):337-352.

Mattson MP., "Cellular actions of beta-amyloid precursor protein and its soluble and fibrillogenic derivatives", Physiological reviews, Oct. 1997; 77(4):1081-1132.

Mattson MP., "Secreted forms of beta-amyloid precursor protein modulate dendrite outgrowth and calcium responses to glutamate in cultured embryonic hippocampal neurons", J. Neurobiol. Apr. 1994; 25(4):439-450.

Mayer S, et al., "Acamprosate has no effect on NMDA-induced toxicity but reduces toxicity induced by spermidine or by changing the medium in organotypic hippocampal slice cultures from rat", Alcohol Clin Exp Res, May 2002; 26(5):655-662.

McCaffery P, et al., "Macrocephaly and the control of brain growth in autistic disorders", Prog Neurobiol., Sep.-Oct. 2005; 77(1-2):38-56.

McFarlane HG, et al., "Autism-like behavioral phenotypes in BTBR T+tf/J mice. Genes Brain Behay", Mar. 2008; 7(2):152-163.

Moy, SS, et al., "Mouse behavioral tasks relevant to autism: phenotypes of 10 inbred strains", Behav Brain Res. Jan. 10, 2007; 176(1):4-20.

Mullan M, et al., "Genetic and molecular advances in Alzheimer's disease," Trends Neurosci., Oct. 1993; 16(10):398-403.

Naassila M, et al., "Mechanism of action of acamprosate. Part I. Characterization of spermidine-sensitive acamprosate binding site in rat brain", Alcohol Clin Exp Res., Jun. 1998; 22(4):802-809.

Niebroj-Dobosz I, et al., "Effect of Riluzole on serum amino acids in patients with amyotrophic lateral sclerosis", Acta Neurol Scand., Jul. 2002; 106(1):39-43.

Orser BA, et al., "Multiple mechanisms of ketamine blockade of N-methyl-D-aspartate receptors", Anesthesiology. Apr. 1997; 86(4):903-917.

(56) References Cited

OTHER PUBLICATIONS

Palucha-Poniewiera A, et al., "Involvement of mGlu5 and NMDA receptors in the antidepressant-like effect of acamprosate in the tail suspension test", Prog Neuropsychopharmacol Biol Psychiatry, Oct. 1, 2012; 39(1):102-106.
Papolos DF, et al., "Clinical experience using intranasal ketamine in the treatment of pediatric bipolar disorder/fear of harm phenotype", J Affect Disord, May 2013; 147(1-3):431-436.
Posey D, et al., "A double-blind, placebo-controlled study of D-Cycloserine in children with autistic disorder", Presentation at: 55th Annual Meeting of the American Academy of Child and Adolescent Psychiatry 2008; Chicago, Illinois, 2 pgs.
Prevention CfDCa. Autism Spectrum Disorder, Data and Statistics. 2014; http://www.cdc.gov/ncbddd/autism/data.html.
Priller C, et al., "Synapse formation and function is modulated by the amyloid precursor protein", J Neurosci., Jul. 5, 2006; 26(27):7212-7221.
Rainey, L., et al., "The anaesthetic management of autistic children", Anesthesia and Intensive Care, Sydney, AU, vol. 26, No. 6, Dec. 1, 1998, pp. 682-686, XP009183694.
Ray, B., et al., "Increased secreted amyloid precursor protein-alpha (sAPPalpha) in severe autism: proposal of a specific, anabolic pathway and putative biomarker", PLoS ONE. 2011; 6(6):e20405.
Schubert, D., et al., "The regulation of amyloid beta protein precursor secretion and its modulatory role in cell adhesion", Neuron. Dec. 1989; 3(6):689-694.
Seeman P, et al., "Memantine agonist action at dopamine D2High receptors", Synapse. Feb. 2008; 62(2):149-153.
Silverman JL, et al., "Ampakine enhancement of social interaction in the BTBR mouse model of autism", Neuropharmacology, Jan. 2013; 64:268-282.
Silverman JL, et al., "Repetitive self-grooming behavior in the BTBR mouse model of autism is blocked by the mGluR5 antagonist MPEP", Neuropsychopharmacology, Mar. 2010; 35(4):976-989.
Sokol DK, et al., "Autism, Alzheimer disease, and fragile X: APP, FMRP, and mGluR5 are molecular links", Neurology. Apr. 12, 2011; 76(15):1344-1352.
Sokol DK, et al., "High levels of Alzheimer beta-amyloid precursor protein (APP) in children with severely autistic behavior and aggression", J Child Neurol., Jun. 2006; 21(6):444-449.
Sparks BF, et al., "Brain structural abnormalities in young children with autism spectrum disorder", Neurology, Jul. 23, 2002; 59(2):184-192.
Stein TD, et al., "Genetic programming by the proteolytic fragments of the amyloid precursor protein: somewhere between confusion and clarity", Reviews in the neurosciences. 2003; 14(4):317341.

The Interagency Autism Coordinating Committee. 2010 Strategic Plan for Autism Spectrum Disorder Research. NIH Publication No. 10-7573: Department of Health & Human Services USA; 2010.
Tottenham, N., et al., "Categorization of facial expressions in children and adults: establishing a larger stimulus set", Cognitive Neuroscience Society Annual Meeting, 2002.
Tottenham, N. et al., "The NimStim set of facial expressions: Judgments from untrained research participants", Psychiatry Research, Elsevier Ireland Ltd., IE, vol. 168, No. 3, Aug. 15, 2009, pp. 242-249, XP026322365.
Turner PR, et al., "Roles of amyloid precursor protein and its fragments in regulating neural activity, plasticity and memory", Prog Neurobiol., May 2003; 70(1):1-32.
Uenishi H, et al., "Ion channel modulation as the basis for neuroprotective action of MS-153", Ann N Y Acad Sci., 1999; 890:385-399.
Wang, SJ, et al., "Mechanisms underlying the riluzole inhibition of glutamate release from rat cerebral cortex nerve terminals (synaptosomes)", Neuroscience, 2004;125(1):191-201.
Weng N, et al., "Early-phase ERK activation as a biomarker for metabolic status in fragile X syndrome", Am J Med Genet B Neuropsychiatr Genet., Oct. 5, 2008; 147B(7):1253-1257.
Westphalen RI, et al., "Selective depression by general anesthetics of glutamate versus GABA release from isolated cortical nerve terminals", J Pharmacol Exp Ther., Mar. 2003; 304(3):1188-1196.
Wink LK, et al., "Pharmacologic treatment of behavioral symptoms associated with autism and other pervasive developmental disorders", Curr Treat Options Neurol., Nov. 2010; 12(6):529-538.
Wink, LK, et al., "Intranasal ketamine treatment in an adult with autism spectrum disorder", The Journal of Clinical Psychiatry Aug. 2014, vol. 75, No. 8, Aug. 2014, pp. 835-836, XP009183695.
Wong SW, et al., "Dilated common bile ducts mimicking choledochal cysts in ketamine abusers", Hong Kong Med J. Feb. 2009; 15(1):53-56.
Yang, M, et al., "Social deficits in BTBR T+tf/J mice are unchanged by cross-fostering with C57BL/6J mothers", Int J Dev Neurosci., Dec. 2007; 25(8):515-521.
Young-Pearse TL, et al., "A critical function for beta-amyloid precursor protein in neuronal migration revealed by in utero RNA interference", J Neurosci., Dec. 26, 2007; 27(52):14459-14469.
Zarate CA, Jr., et al., "A randomized trial of an N-methyl-D-aspartate antagonist in treatment-resistant major depression", Arch Gen Psychiatry., Aug. 2006; 63(8):856-864.
Zarate CA, Jr., et al., "Replication of ketamine's antidepressant efficacy in bipolar depression: a randomized controlled add-on trial", Biol Psychiatry., Jun. 1, 2012; 71(11):939-946.
International Search Report and Written Opinion dated May 7, 2015 for Application No. PCT/US2015/011412.
U.S. Appl. No. 61/926,991, filed Jan. 14, 2014.
U.S. Appl. No. 62/059,306, filed Oct. 3, 2014.

* cited by examiner

COMPOSITIONS AND METHODS FOR TREATING AN AUTISM SPECTRUM DISORDER

CROSS REFERENCE TO RELATED APPLICATIONS

This application claims priority to and benefit of U.S. Provisional Application Ser. No. 61/926,991, filed Jan. 14, 2014, and U.S. Provisional Application Ser. No. 62/059,306, filed Oct. 3, 2014, the contents of which are incorporated herein in their entirety for all purposes.

BACKGROUND

Over the last decade there has been a sharp rise in reported cases of Autism Spectrum Disorder (ASD) with a recent U.S. CDC prevalence estimate of 1 in 88 children diagnosed with ASD. Children diagnosed with an ASD have resultant medical expenditure 4-6 times greater than typically developing peers, and endure lifelong deficits in social communication and interaction and restricted patterns of behavior or interests. They often also exhibit associated symptoms including hyperactivity and irritability. Despite extensive pharmaceutical research, there are no FDA-approved medications for treatment of the core social impairment associated with ASD. Several factors have contributed to the slow development of targeted core impairment pharmacotherapy including the heterogeneous clinical presentation of ASD and limited availability of objective outcome measures of social/communication improvement. There remains a clear gap in the knowledge base of effective drug treatment of core social and communication impairment in ASD.

BRIEF SUMMARY

Disclosed are compositions and methods for the treatment of a subject having an autism spectrum disorder. The disclosed compositions may contain racemic ketamine or S-ketamine. The disclosed methods of administering the compositions include intranasal administration to a subject having autism spectrum disorder.

DETAILED DESCRIPTION

Definitions

Figure 1:
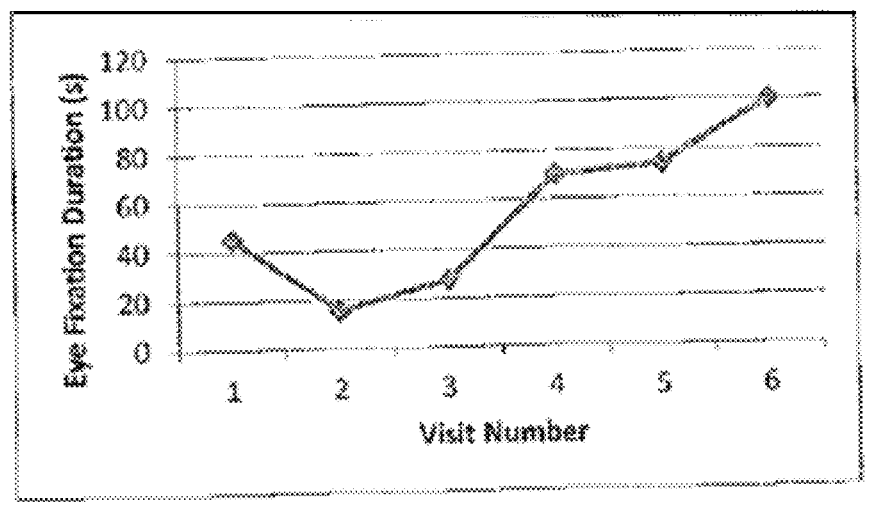
FIG. 1 depicts a graph showing clinical eye tracking data employing the NimStim Stimulous set measuring the length of gaze fixation on the eye region of fearful, happy, or calm facial expression, which significantly increased over the course of treatment in the patient described in Example 3.

The terms and expressions used herein have the ordinary meaning as is accorded to such terms and expressions with respect to their corresponding respective areas of inquiry and study except where specific meanings have otherwise been set forth herein.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "individual," "host," "subject," and "patient" are used interchangeably to refer to an animal that is the object of treatment, observation and/or experiment. "Animal" includes vertebrates and invertebrates, such as fish, shellfish, reptiles, birds, and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans.

The term "effective amount" means the amount of the formulation that will be effective in the treatment of a particular subject will depend on the particular subject and state of the subject, and can be determined by standard clinical techniques. In addition, in vitro or in vivo assays may optionally be employed to help identify optimal dosage ranges. The precise dose to be employed will also depend on the state of the patient, and should be decided according to the judgment of the practitioner and each patient's circumstances.

The term "pharmaceutically acceptable" means approved by a regulatory agency of the Federal or a state government or listed in the U.S. Pharmacopeia or other generally recognized pharmacopeia or otherwise proven as safe for use in animals, mammals, and more particularly in humans.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. Pharmaceutically acceptable carriers include a wide range of known diluents (i.e., solvents), fillers, extending agents, binders, suspending agents, disintegrates, surfactants, lubricants, excipients, wetting agents and the like commonly used in this field. These carriers may be used singly or in combination according to the form of the pharmaceutical preparation, and may further encompass "pharmaceutically acceptable excipients" as defined herein.

The term "social engagement," as used herein, is synonymous with social relatedness, i.e., one's interest in social activity, the ability and interest in engaging in social situations, engaging with social stimuli etc. In looking at faces, social engagement is represented by majority gaze at the eyes, something that is substantially lacking in persons with autism/ASD.

The glutamate N-methyl-D-aspartate (NMDA) receptor antagonist ketamine, has been demonstrated in controlled clinical trials to rapidly decrease symptoms of depression in individuals with major depression and bipolar depression via intravenous infusion and/or IM. Zarate, C. A., Jr., et al., A randomized trial of an N-methyl-D-aspartate antagonist in treatment-resistant major depression. Arch Gen Psychiatry, 2006. 63(8): p. 856-64; Zarate, C. A., Jr., et al., Replication of ketamine's antidepressant efficacy in bipolar depression: a randomized controlled add-on trial. Biol Psychiatry, 2012. 71(11): p. 939-46. Intranasal (IN) administration in adolescents has been explored with bipolar disorder with promising results. Papolos, D. F., et al., Clinical experience using intranasal ketamine in the treatment of pediatric bipolar disorder/fear of harm phenotype. J Affect Disord, 2013. 147(1-3): p. 431-6. To date, however, there have been no published reports of ketamine treatment in individuals with ASD. Further, while ketamine has been suggested as a possible treatment for autism, such teachings are limited to the use of levels of ketamine at such high levels so as to induce an anesthetic effect. (Zimmerman, U.S. Pat. No. 4,994,467.) Such levels are dangerously high for nonessential use and impractical for treatment of individuals with this disorder due to the high risks involved at such dosage levels. Further, there has been no evidence to date that low levels of ketamine could be administered intranasally to achieve a positive effect in patients having ASD, nor would such a result be expected in view of the knowledge in the art.

While a detailed understanding of the pathophysiology of ASD has not yet been developed, dysregulation of glutamate neurotransmission has been consistently implicated as playing a potential role in ASD. Glutamate is the primary excitatory neurotransmitter and glutamate plays a role in neuronal development and synaptic plasticity. Recent studies have identified abnormal peripheral glutamate levels, aberrant glutamate expression in post mortem brain, and genetic abnormalities in glutamate signaling genes in individuals with ASD[3]. Attenuation of N-methyl-D aspartate (NMDA) specific glutamate neurotransmission has been the subject of significant drug development efforts to date in ASD. The use-dependent inhibitors of NMDA neurotransmission d-cycloserine (DCS), amantadine, and memantine have all been subject of study in ASD. DCS and amantadine were both subjects of negative placebo-controlled trials in ASD[4,8]. Results of an industry sponsored placebo-controlled study of memantine in ASD remain undisclosed. The irritability promoting effects of memantine in ASD has been reported,[6,7] due likely to memantine's additional action as a dopamine D2 receptor agonist[8].

Ketamine (2-(2-chlorophenyl)-2-(methylamino)-cyclohexanone) is an FDA-approved anesthetic agent used since the 1970s via intravenous intramuscular (IM) administration for rapid induction of dissociative anesthesia. Ketamine is a unique non-competitive NMDA antagonist which blocks the open NMDA channel to decrease channel open time and also uses allosteric modulation to reduce mean channel opening frequency 8. Ketamine has also been shown to enhance glutamate-induced maturation of synaptic networks and synaptic plasticity in preclinical models[10]. Ketamine has additionally been demonstrated in clinical trials to provide rapid relief of depression in adults via single intravenous dose[11]. Historically, the use of ketamine for clinical treatment has been limited by intravenous dosing. However, recently intranasal (IN) ketamine has been investigated for use in children with bipolar disorder. Emerging evidence supports the use of IN ketamine for treatment of mood, anxiety, and aggressive symptoms in children with bipolar disorder[12]. To date, no studies have investigated the use of ketamine in ASD.

Ketamine has a unique pharmacodynamic profile clearly differentiated from other glutamatergic modulators studied in ASD to date. This profile coupled with ketamine's long safety track record and novel IN delivery system, make ketamine the essential next step in pharmacologic investigation for treatment of the core features of ASD. As a generically available inexpensive drug, ketamine holds significant promise to widely treat the core social and communication impairments that are the hallmark of ASD. The development of IN ketamine for use in ASD addresses the significant gap in the knowledge base of effective ASD pharmacology while utilizing a drug with a demonstrated safety profile that is poised for widespread cost-effective usage across the lifespan.

A lack of quantitative and objective measure of core social impairment has plagued previous drug treatment development in ASD. Our group has addressed this short coming of ASD drug study by working with a novel measure of aberrant social preference. Applicant has developed a one minute social preference eye tracking task in youth and young adults with ASD that has demonstrated reduced preference in persons with ASD for viewing social scenes of interacting people versus viewing of moving geometric objects (social/geometric viewing ratio in persons with ASD=2.3 versus 3.9 for persons without ASD; p=0.03)[14]. It is believed that this novel quantitative eye tracking task will provide an objective means to assess change in social preference with treatment in ASD research.

Biomarkers in ASD research hold promise to both aid understanding of the pathophysiology of ASD, and act as markers/predictors of targeted treatment response[15]. Extracellular signal-related kinase (ERK) is a nodal point for several signaling cascades, and numerous recent findings link potential ERK dysregulation to the pathophysiology of idiopathic ASD[16-20]. Conditional ERK isoform 2 (ERK2) knockout mice have been shown to exhibit several features of relevance to ASD including reduced social behavior, deficits in nest-building, and memory deficits21. Deletion at chromosome 16p11.2 on which ERK1 is located,[19] and deletion at chromosome 22q11.2, where the gene for ERK2 is located,[18,20] have been associated with ASD. ERK signaling activity has been shown to be upregulated in the BTBR mouse model of autism[17]. In post-mortem study, the protein expression and activities of both ERK1 and ERK2 isoforms have been shown to be upregulated in the frontal cortex of persons with autism[16].

Aberrant ERK activity has also been noted in Fragile X Syndrome (FXS), a common single gene cause of ASD (2 in 3 males with FXS meet ASD criteria)[22-24]. Recently, ERK activation has been shown to be delayed in the peripheral lymphocytes of humans with FXS[25,26]. In addition to FXS, aberrant ERK regulation is evident in other defined disorders associated with ASD including tuberous sclerosis and neurofibromatosis type 1[27].

Among biological factors associated with ASD, macrocephaly is a consistently replicated finding affecting up to 20% of children with autism[28-30]. Brain magnetic resonance imagery (MRI) studies in ASD have noted abnormal total brain volume enlargement in infants and toddlers[31-34]. Furthermore, early brain enlargement marked by increased surface area overgrowth seen in youth with autism may be associated with a disruption in cell adhesion[35]. Among factors contributing to the brain overgrowth theory of ASD, pathophysiology, the potential contribution of dysregulation in amyloid-β precursor protein (APP) metabolism has been proposed[36-39]. APP has been associated with Alzheimer's disease (AD) where the amyloidogenic pathway of APP processing favors cleavage of APP by β-site APP cleaving enzyme or β-secretase (BACE1) resulting in neurotoxic amyloid-β (Aβ) peptides consisting 40 and 42 amino acids residues[40]. Aβ40 and Aβ42 are the major components of senile plaques associated with brain atrophy in AD. APP is predominantly located at the synapse[41], produced in brain microglia, astrocytes, oligodendrocytes, and neurons[42], and released in an activity driven fashion43. Activation of metabotropic glutamate receptor type 1 and type 5 (mGluR1/5) increases APP secretion in cell culture[43]). The highest levels of APP occur early in synaptogenesis44 and peak before 1 month of age in rodents45. APP has been implicated in neurite outgrowth[41,42] and promotes growth cone development working in opposition to N-methyl-D-aspartate) NMDA and (α-amino-3-hydroxy-5-methyl-4-isoxazolepropionic acid) AMPA glutamate receptors' pruning effects on growth cones[41]. As shown in cell culture studies, APP may block and reverse glutamatergic inhibition of dendrite outgrowth[46]. APP has been linked to suppression of neuronal cell adhesion[47] and overexpression of APP accelerates migration of neuronal precursor cells into the cortex[48]. The non-amyloidogenic APP processing pathway involving cleavage by the α-secretase family of enzymes (such as ADAM 9, 10 and 17) is the predominant APP processing pathway leading to release of non-amyloidogenic secreted APPα (sAPPα)[37,46]. Several reports have noted neurotrophic effects of sAPPα, including activity in inducing cellular proliferation including the proliferation of neural progenitor cells[49-51]. Notably, sAPPα also activates microglia[52]. Overall, APP and specifically sAPPα are prime candidates to contribute to synaptic disruption and brain overgrowth in ASD given the proteins' enhancement of neural proliferation. APP modulation and A□ have been shown to be a target of several drugs, including cholinesterase inhibitors and a partial NMDA receptor antagonist (memantine)[53-55].

There have been several reports on abnormalities in secreted APP and specifically sAPPα in the blood of youth with autism including significant work completed by Applicant in collaboration with the lab of Deb Lahiri PhD at Indiana University[36-38, 56]. Higher levels of total plasma sAPP and sAPPα were identified in a small sample of young children with autism and aggressive behavior compared to less impaired youth with autism without aggressive behavior and control subjects[38]. In a follow-up report involving 16 youth with autism and 18 control subjects, a similar increase in sAPPα was found in children with severe autism compared to youth with milder cases of autism and neurotypical control subjects[37]. In the same study, reduced levels of Aβ40 and Aβ42 were identified in the youth with severe autism compared to control subjects. In a a study involving 25 youth with autism aged 2-5 years and matched control subjects mean plasma sAPPα was significantly elevated in those with autism; 60% of those with autism had elevations in sAPPα[56]. Considering these results together, elevation in plasma sAPP (total) and specifically sAPPα could be a marker of molecular dysregulation contributing to the pathophysiology of autism.

Current pharmaceutical compositions of ketamine are racemic mixtures of S- and R-ketamine, though S-ketamine has been found to be two to three times as potent as R-ketamine than the racemic mixture. (See, e.g., EP 1567145 B1.) S ketamine is also used in foreign countries as an IV anesthetic, under the following trade names: Ketanest S, Ketanest-S, Keta-S, and S-Ketamin Pfizer.

Applicant has surprisingly found that Ketamine, in intranasal form, is capable of mitigating the effects of autism in humans. In particular, Applicant has found a beneficial effect with respect to behavioral aspects in patients having ASD in response to intranasal administration of ketamine. Additionally, the Applicant has noted similar mitigation of behaviors associated with autism in a mouse model of autism.

In one aspect, a method of treating an autism spectrum disorder in a subject in need thereof is disclosed. The method may comprise the step of intranasally administering a composition comprising ketamine and a pharmaceutically acceptable excipient and/or carrier to said subject in need thereof.

In one aspect, the composition may comprise racemic ketamine. In one aspect, the composition may comprise S-ketamine. In one aspect, the composition may comprise greater than about 50%, or greater than about 60%, or greater than about 70%, or greater than about 80% or greater than about 90%, or greater than about 95%, or greater than 99% of the S enantiomer of ketamine. In one aspect, the composition may be substantially free of R-ketamine.

In certain aspects, the composition may comprise a second active agent. For example, the composition may further comprise an agent for treating autism. Such agents may include any such agent known in the art, for example, atypical antipsychotics, stimulants, serotonin reuptake inhibitors, alpha 2 agonists, or combinations thereof.

In one aspect the composition may be administered weekly. In other aspects, the composition may be administered every two to seven days, or, in other aspects, on a daily basis. The composition may be administered in an escalating dose.

In one aspect, the said dose administered may comprise from about 20 to about 120 mg ketamine, or from about 50 to about 100 mg, or from about 70 to about 80 mg. Suitable dosages may be determined on a mg/kg basis. For example, the dosage may be from about 0.25 mg/kg to about 3 mg/kg, or from about 0.5 mg/kg to about 2 mg/kg, or from about 0.75 mg/kg to about 1.5 mg/kg, or about 1 mg/kg. Such dosage may be administered at regular intervals, for example daily, weekly, or every 1 to 7 days, every 2 to 6 days, every 3 to 5 days, or any combination thereof. The dosage may vary among individuals and may generally be a weekly dose with a supplemental dosage as needed.

The compositions disclosed herein may further comprise other agents suited for improved delivery across nasal mucosa. For example, in certain aspects, agents such as a permeation enhancer, a polymer capable of increasing mucosal adhesion of the composition, or a combination thereof may be included in the composition.

In one aspect, an intranasal delivery device comprising a composition comprising ketamine, preferably S-ketamine, and a pharmaceutically acceptable carrier, is disclosed. The composition of the device may comprise any composition as described above.

In one aspect, methods of improving social engagement are disclosed, comprising the step of administering a composition as described herein to a subject having autism/ASD, wherein said administration step is via intranasal administration.

In one aspect, a method of measuring treatment response comprising the step of using Nim Stim faces as a measure of change in social relatedness is disclosed. Given that reduced viewing of eyes has been frequently reported in persons with autism and that this reduction is an accepted measure of reduced social relatedness, viewing of eye regions pre- and post-ketamine treatment using a selection of faces from the Nim Stim set can be assessed.

EXAMPLES

Example 1

Ketamine is compounded into a mucosal atomization device which delivers 20 mg of atomized ketamine per 0.1 cc spray. The subject will self-administer (or administer with the help of a caregiver) ketamine every four to seven days. On the first administration, 2 sprays are administered. On subsequent administration days, one spray will be added to the dosage, unless the subject reaches treatment response as described herein. Where a treatment response is obtained, the dose will remain constant at this minimally effective dose throughout treatment. If an adverse effect is observed, the dose will be decreased to a previous tolerable dose for the remainder of treatment.

Treatment response is defined as a score of 1 "very much" or 2 "much improved" on the CGI Improvement scale (CGI-I) and 0.25% improvement on the ABC-SW. Additional subject and/or caregiver report measures will include the Social Responsiveness Scale (SRS), Anxiety Depression and Mood Scale (ADAMS), Yale-Brown Obsessive Compulsive Scale for pervasive developmental disorders (YBOCS-PDD), and CGI-S. All measures will be completed at baseline and each visit.

Eye tracking will be completed using a Tobil T120 hands free eye tracker as previously done by our group. Subjects will view videos of social interaction positioned next to video of moving geometric objects, as well as picture of emotional faces lasting a total of 5 minutes, eye tracking output will be reported as the ratio of social versus geometric viewing time and mean length of gaze fixation on eye, nose, and mouth regions of emotional faces. Eye tracking will be completed at baseline and each visit prior to drug dosing.

Example 2

Ketamine is compounded into a mucosal atomization device which delivers 20 mg of atomized ketamine per 0.1 cc spray. The subject will self-administer (or administer with the help of a caregiver) ascending doses of 20 mg at week 1, 40 mg week 2, 60 mg week 3, 80 mg week 4, unless the subject reaches treatment response as described above or experiences adverse effect prior to reaching 80 mg dose. In case of treatment response, dose will remain constant at the minimally effective dose throughout treatment. In case of an adverse event, the dose will be decreased to the previous tolerable dose.

Example 3

The patient is a 29-year-old woman with ASD, Anorexia Nervosa, Obsessive-Compulsive Disorder, and Major Depressive Disorder. She has a 15 year history of debilitating psychiatric illness, with over 30 psychotropic medication trials, multiple psychiatric hospitalizations, residential treatment, electroconvulsive therapy, weight restoration therapy, and one suicide attempt. Symptoms at presentation included social impairment, repetitive behaviors, need for sameness, sensory sensitivity, contamination fears, low weight, absent menstrual cycles, chronic purging, depressed mood, anhedonia, low energy, poor concentration, and chronic suicidality. Daily medications included selegiline transdermal, lamotrigine, naltrexone, and clonazepam. Despite extensive treatment, she remained significantly disabled and had recently taken a medical leave from graduate school. After discussion of the potential risks, the patient elected to undergo IN ketamine treatment.

Baseline comprehensive assessment included clinical interview completed by psychiatrist with expertise in ASD (LKW), the Autism Diagnostic Observation Schedule-2 (ADOS) Module 4 performed by research reliable psychologist (RCS), vital signs, electrocardiogram (EKG), complete blood count, and comprehensive metabolic panel. Ketamine nasal spray compounded to deliver 20 mg per 0.1 cc spray was obtained from a compounding pharmacy. All visits took place in an outpatient psychiatric clinic, with visits for IN ketamine administration on days 1, 7, 14, 17, and 21. Prior to medication administration at each visit the Montgomery-Asberg Depression Rating Scale (MADRS), Beck's Depression Inventory (BDI), Yale-Brown Obsessive Compulsive Scale (Y-BOCS), Eating Attitudes Test (EAT-26), and an eye-tracking paradigm of emotional faces from the NimStim Stimulus Set were completed. Tottenham, N., et al., Categorization of facial expressions in children and adults: establishing a larger stimulus set. Cognitive Neuroscience Society Annual Meeting, 2002. Following medication administration, vital signs were monitored for 60 minutes. Additionally, the MADRS and BDI were completed at irregular intervals between visits.

At baseline, clinical interview and ADOS-2 confirmed the ASD diagnosis. Vital signs, labs, and EKG revealed no abnormalities except low weight (BMI=15). MADRS score was 44 and BDI 35 indicating severe depression symptoms. Y-BOCS subscales were significantly elevated. EAT-26 score indicated significant eating disorder symptoms.

The patient self-administered 20 mg of IN ketamine on day 1 of treatment, and 40 mg on days 7, 14, 17, and 21. Dosage increase between day 1 and 7 was based on tolerance of starting dose and resultant brief but significant improvement in mood. Dosing frequency was increased to every 3 days based on return to baseline mood at 3-4 days post doses 1, 7, and 14. Immediately following administration of ketamine, the patient reported transient sedation, dizziness, numbness of limbs and face, and blurred vision lasting approximately 90 minutes post-dose. Blood pressure, heart rate, and temperature were stable throughout. She experienced mild headaches lasting 6-10 hours following each dose. The patient reported significant improvement in mood and had dramatically improved BDI and MADRS scores within 24 hours following each dose. She also reported increased ease of interacting with others, reduced urge to purge, and more flexibility and tolerance of routine change. Of note, on day 2 she agreed to inpatient treatment of her eating disorder, treatment she had refused for months previous to ketamine administration. This was seen by her treatment team as a sign of improved outlook and reduced rigidity in her thinking. The patient remained hospitalized throughout the remainder of the treatment described herein.

Between visits on day 21 and 43, the patient continued to self-administer IN ketamine outside of our clinic. Dosage was increased to 60 mg on day 30 due to perceived diminished response to the previous dose. The patient continued to tolerate ketamine without difficulty. On day 43, she reported significantly improved mood, increased motivation, improved concentration, decreased suicidal thoughts, and feeling more connected to others. MADRS and BDI scores continued to improve significantly (Day 43 MADRS=15; Day 43 BDI=5). Additionally, eye tracking data measuring the length of gaze fixation on the eye region of faces demonstrating fearful, happy, or calm expressions significantly increased over the course of treatment (FIG. 1). Repeat ADOS at six weeks demonstrated no change in ADOS score, although subjectively the administrator felt the patient was more engaging. There was little change in Y-BOCS or EAT-26 scores throughout treatment.

In conclusion, this complicated patient with significant developmental and psychiatric illness was observed to experience notable improvement in depression symptoms with IN ketamine treatment. Additionally, significant change was noted on the eye tracking paradigm with treatment. Individuals with ASD tend to spend less time viewing the eye region of emotional faces than typical peers, and the significant increase in this patient's fixation duration suggests improved social interest. Falck-Ytter, T., S. Bolte, and G. Gredeback, *Eye tracking in early autism research.* J Neurodev Disord, 2013. 5(1): p. 28. This finding is not explained by relief of her depression symptoms, as with symptomatic improvement depressed individuals tend to spend less time viewing dysphoric stimuli. Armstrong, T. and B. O. Olatunji, Eye tracking of attention in the affective disorders: a meta-analytic review and synthesis. Clin Psychol Rev, 2012. 32(8): p. 704-23. On the contrary, this patient demonstrated increased duration of fixation on the eye region of fearful faces with improvement in depression symptoms. This is a key finding in an individual with ASD, suggesting potential treatment of core social impairment with ketamine. This work is limited due to the single and complicated patient. However, IN ketamine's overall tolerability coupled with significant mood improvement and potential change in social interest suggest the usefulness of ketamine for treatment in the ASD population.

Example 4

A second patient clinically treated with intranasal ketamine was a 15-year-old male with Autistic Disorder. This patient was treated with an Initial dose of 20 mg, with subsequent 40 gm doses weekly for the following 3 weeks. This patient experienced minor sedation, but otherwise tolerated ketamine well.

Figure 2:
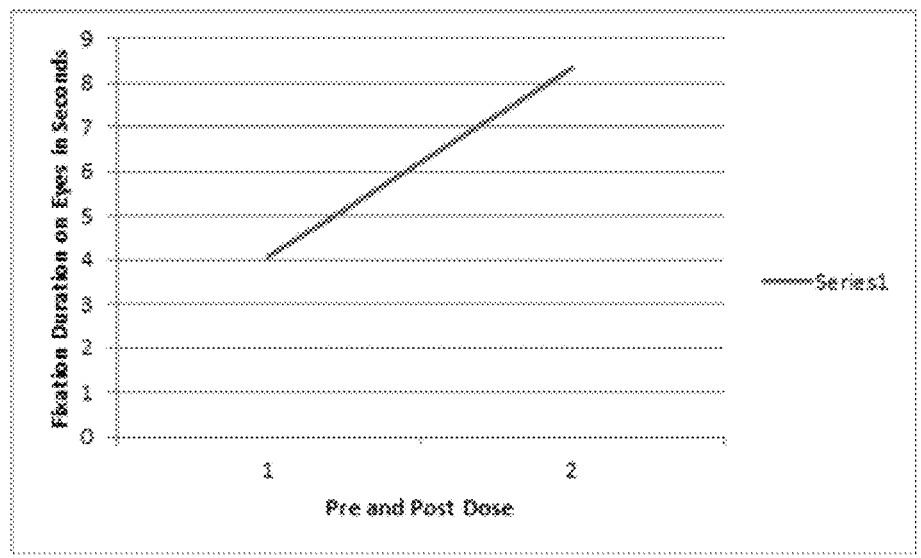
FIG. 2 depicts a graph of Fixation Duration on Eyes in Seconds, Pre and Post Dose, Pre-dose: 4.09, Post-dose: 8.33 per Example 4.
Figure 3:
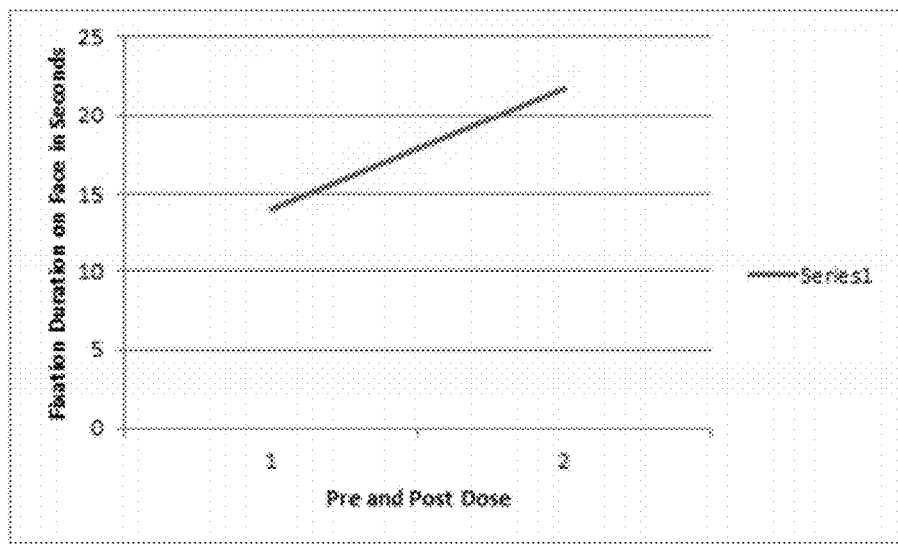
FIG. 3 depicts a graph of Fixation Duration on Face in Seconds, Pre and Post Dose, Pre-dose: 14.01, Post-dose: 21.7 per Example 4.

This patient has the pre and post dose eye tracking data, before and after 40 mg intranasal ketamine doses given weekly as shown in FIGS. 2 and 3. In FIG. 2, pre-dose: 4.09; post-dose: 8.33. In FIG. 3, pre-dose: 14.01; post-dose: 21.7. From the NimStim stimuli set, twelve faces are presented in four sets of three faces separated by 20 second videos. Each face is preceded by a scrambled face. There are 3 randomly dispersed emotions of fear, happy, and neutral with each presented four times. Gender changes with each face.

Example 5

A third patient clinically treated with intranasal ketamine was a 17-year-old male with Autistic Disorder. This patient was treated with an Initial dose of 20 mg one time to date.

Figure 4:
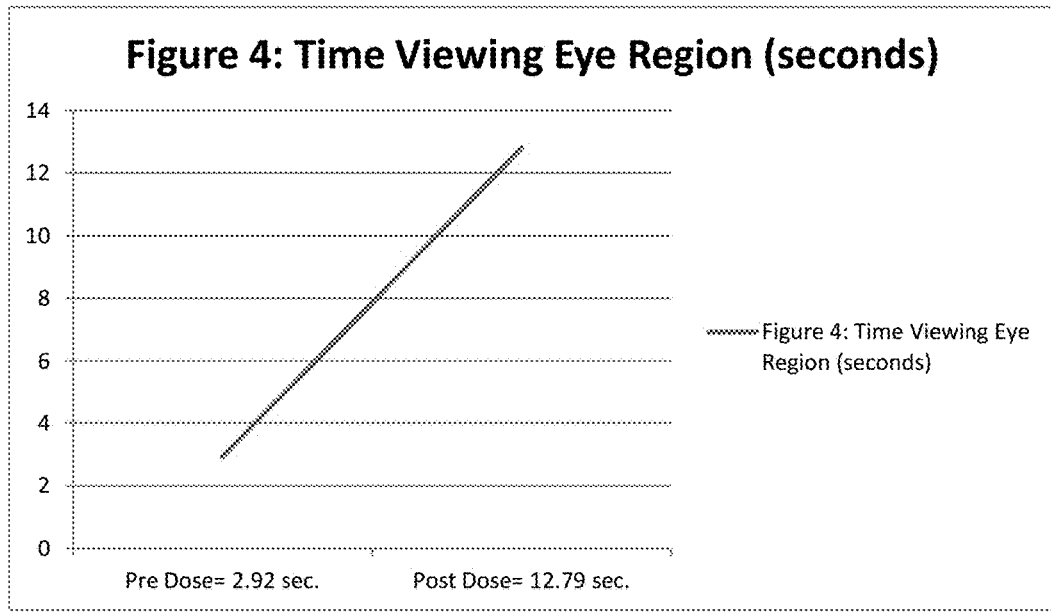
FIG. 4 depicts a graph of Fixation Duration on Eyes in Seconds, Pre and Post Dose, Pre-dose: 2.92, Post-dose: 12.79 per Example 5.
Figure 5:
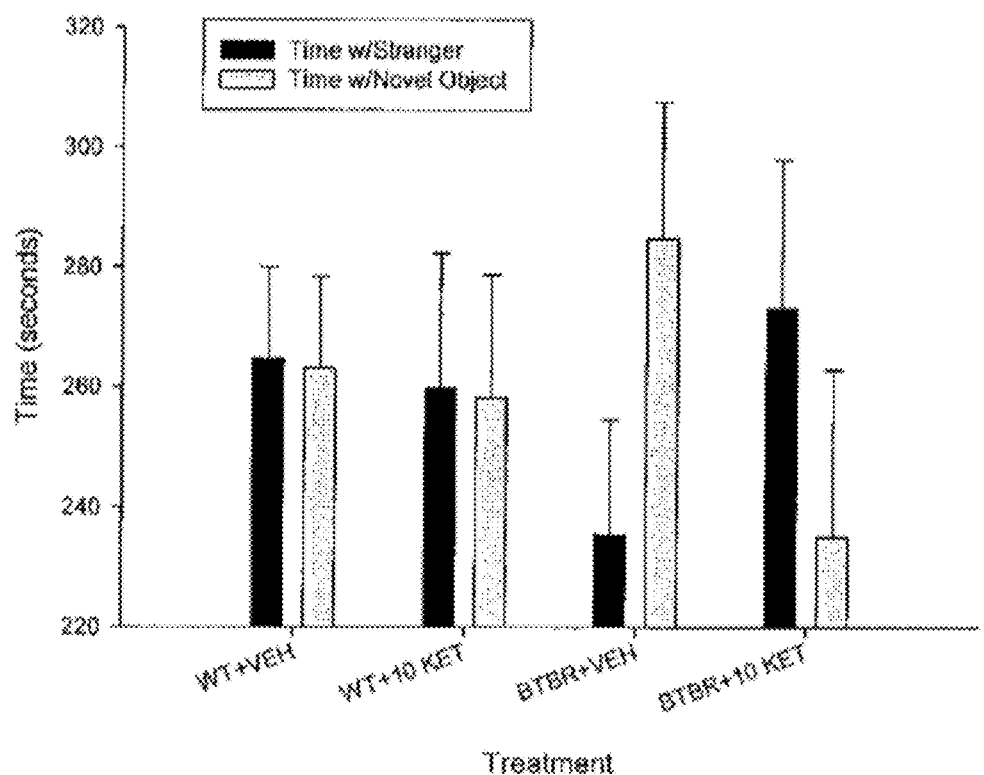
FIG. 5 depicts the Chamber Social Test Results of Example 6.

This patient has the pre and post dose eye tracking data, before and after the initial 20 mg intranasal ketamine dose given as shown in FIG. 4. In FIG. 4, pre-dose viewing of eye region: 2.92; post-dose: 12.79. From the NimStim stimuli set, twelve faces are presented in four sets of three faces separated by 20 second videos. Each face is preceded by a scrambled face. There are 3 randomly dispersed emotions of fear, happy, and neutral with each presented four times. Gender changes with each face. The results viewing the eye region was striking 1 hour post-dose.

Example 6

Female B6 (WT; control) and BTBR mice (autism model) were mated with males of their respective strains. Pups from these mating strategy were used as subjects. At postnatal day 60 mice were either dosed with a saline vehicle (VEH) or 10 mg/kg racemic ketamine HCL (10 KET) once weekly for 5 weeks. On the 5th week mice were tested in the 3 Chamber Social Test 24 h following dosing. Mice were acclimated to the center chamber for 5 minutes and then allowed to explore all three empty chambers for 10 minutes. The test phase followed immediately in which a stranger mouse contained inside a metal bar chamber (stranger) was placed in one side chamber and an empty chamber (novel object) was placed in the other outside chamber. The VEH exposed BTBR mice avoided the chamber containing the stranger mouse which is a behavior typically reported in the literature and reminiscent of autism like social avoidance or disinterest. The ketamine exposed BTBR mice appear to have an increased preference for the stranger mouse in this cohort. Ketamine did not alter motor behavior in the WT or in the BTBR mice. The Chamber Social Test Results are shown in FIG. 4.

Example 7. Study Protocol 1, Placebo Controlled

To address the significant need for effective treatment of core symptoms of ASD, a double blind, placebo controlled parallel groups pilot study of intranasal (IN) ketamine in 12 individuals with ASD agents 12-30 years using a novel quantitative outcome measure of social impairment is proposed. To develop a ketamine-focused personalized medicine approach in ASD, pharmacokinetic (PK) and molecular pharmacodynamic (PD) assessments may be incorporated into the initial systematic study by addressing the following Specific Aims:

Aim #1: Determine if IN ketamine shows initial evidence of efficacy, safety, and tolerability in individuals with ASD. Without intending to be limited by theory, it is hypothesized that IN ketamine will be safe and show initial signs of efficacy targeting core social impairment in ASD.

Aim #2: To further the development of quantitative and objective measurement of social change in ASD utilizing an eye-tracking paradigm. Without intending to be limited by theory, it is hypothesized that individuals with ASD will exhibit increased preference for viewing social scenes and increased mean length of gaze fixation on the eye region of emotional faces with use of IN ketamine.

Aim #3: To examine the short and longer-term impact of IN ketamine administration on lymphocytic extracellular signal related kinase (ERK) activation and plasma amyloid precursor protein (APP) derivative levels in 12 individuals with ASD. Without intending to be limited by theory, it is hypothesized that ketamine use will be associated with short and longer-term reduction in elevated lymphocytic ERK activation rates and reduction in total APP and sAPPα. It is further hypothesized that IN ketamine use will restore ERK activation rates and plasma APP derivative levels to those consistent with neurotypical peers. The degree of excessive ERK activation and sAPPα elevation at baseline is hypothesized to correlate with the degree of clinical treatment response.

Aim#4: Without intending to be limited by theory, it is hypothesized that IN ketamine administration will exhibit linear pharmacokinetics. Increasing ketamine peak concentration and systemic exposure (as measured by the area under the curve; AUC) will be associated with drug effects, including impact on ERK, tolerability, and clinical response.

Research Design and Methods—Inclusion Criteria

Age ≥12 and <31 years.

Weight greater than 40 kg.

General good health as determined by physical exam, medical history, laboratory work up, and EKG.

DSM-V diagnosis of autism spectrum disorder (not associated with Fragile X Syndrome or other known genetic syndrome) as confirmed by the Autism Diagnostic Observation Schedule (ADOS) at screen or previous (within last 5 years) if available.

Valid IQ score ≥50 as confirmed via testing (Differential Abilities Scale (DAS)) at screen or previous (within last 5 years, any valid testing acceptable).

Clinical Global Impression Scale Severity score (CGI-S) of ≥4 (Moderately Ill)

Score of ≥10 on the Social Withdrawal subscale of the Aberrant Behavior Checklist (ABC-SW) at screen and baseline.

Stable dosing of all concomitant psychotropic medications for five half-lives prior to screening visit and during the study.

Presence of parent/guardian or significant other or caregiver willing to serve as informant for behavioral outcome measures.

Research Design and Methods—Exclusion Criteria

Presence of co-morbid schizophrenia, schizoaffective disorder, bipolar disorder with psychosis, bipolar disorder, or psychosis not otherwise specified. Comorbid diagnoses determined by psychiatrist clinical interview and use of DSM-5 diagnostic criteria.

History of drug or alcohol abuse.

Presence of cardiac disease including coronary artery disease, congestive heart failure, or uncontrolled hypertension per medical history.

History of airway instability, tracheal surgery, or tracheal stenosis per medical history.

Central nervous system masses or hydrocephalus per medical history.

Porphyria, thyroid disorder, thyroid medication use per medical history.

Glaucoma or other cause of increased intraocular pressure per medical history.

Allergy to ketamine.

Current use of drugs with concomitant modification of NMDA glutamate activity (amantadine, memantine, d-cycloserine etc.)

For female subjects of child bearing potential, a positive serum pregnancy test.

Any major chronic medical or chronic respiratory illness identified by medical history and considered to be uncontrolled by the Principal Investigator.

Likely inability to tolerate study procedures or study drug per the discretion of the Principal Investigator.

Study Design

Figure 6:
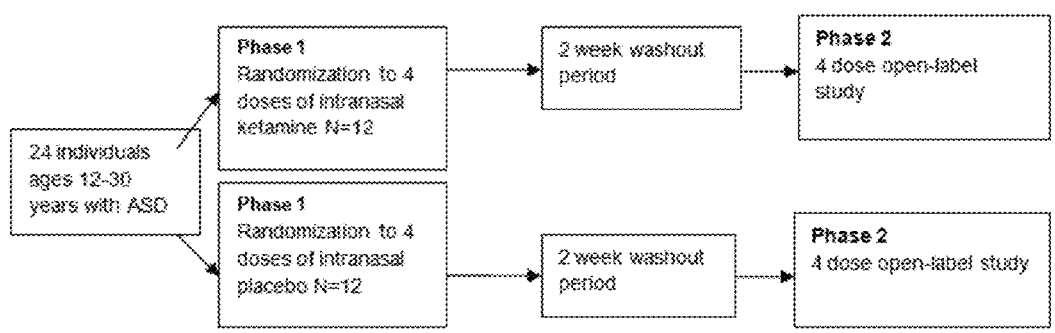
FIG. 6 depicts a schematic of a study involving a randomized double-blind, placebo-controlled parallel group pilot study of four ascending doses of intranasal ketamine with open-label extension.

The proposed study will involve a randomized double-blind, placebo-controlled parallel group pilot study of four ascending doses of intranasal ketamine with open-label extension. See FIG. 6

Study Drug Dosing

Study drug will be administered at research visits, and subjects will remain on site for minimum of 75 minutes post study drug dose. Subjects will not take study drug home with them at any point in the study. All visits will occur at least 4 days apart, with maximum of 8+/−2 days between visits (goal 7 days).

Ketamine will be compounded into a mucosal atomization device which delivers 10 mg of atomized ketamine per 0.1 cc spray. Placebo will deliver 0.1 cc of atomized saline per spray. In Phase 1, participants will self-administer (or administer with the help of a caregiver) 2 sprays at visit 1, 4 sprays at visit 2, 6 sprays at visit 3, and 8 sprays at visit 4, unless subject reaches treatment response (see primary outcome measure below) or experiences significant adverse effect prior to reaching 8 sprays. In case of treatment response, dose will remain constant at minimally effective/tolerated dose throughout remainder of Phase 1. In case of adverse event determined by Primary Investigator to have negative potential impact on the patient's health or safety (see safety information below for discussion of potential adverse effects), dose will be decreased to previous tolerable dose for remainder of Phase 1 or study participation will be terminated depending on the severity and medical relatedness of the adverse effect. Prior to Phase 2, all subjects will undergo a 2 week wash-out period. In Phase 2, all patients will receive active drug in ascending doses of 20 mg at week 1, 40 mg week 2, 60 mg week 3, 80 mg week 4, unless subject reaches treatment response (see primary outcome measure below) or experiences adverse effect prior to reaching 80 mg dose. In case of treatment response, dose will remain constant at minimally effective dose throughout remainder of Phase 2. In case of adverse event, dose will be decreased to previous tolerable dose for remainder of Phase 2 or study participation will be terminated depending on the severity and medical relatedness of the adverse effect.

Blindness and Breaking the Blind

The study blind will be maintained throughout the duration of the clinical trial. Only the Cincinnati Children's Hospital Medical Center Investigational Pharmacy will be aware of study drug assignment. The blind will be broken only at the discretion of a participating study physician or Medical Monitor in cases necessary to assure patient safety. Such significant safety events would include, but are not limited to, any circumstance where an adverse effect documented as possibly, probably, of definitely related to study treatment and moderate or more severe in intensity results in the need for additional medical intervention (hospitalization, emergency/urgent care room visit, additional outpatient prescribing/other management etc.).

Primary and Secondary Outcome Measures

Treatment response will be defined as a score of 1 "very much" or 2 "much improved" on the CGI Improvement scale (CGI-I) and ≥25% improvement on the ABC-SW. A dichotomous definition of treatment response as noted above will serve as the study primary outcome measure. Key secondary continuous outcome measures will be the ABC-SW. Additional subject and/or caregiver reported secondary outcome measures will include the Social Responsiveness Scale (SRS), Anxiety Depression and Mood Scale (ADAMS), Repetitive Behavior Scale-Revised, and CGI-S. All measures will be completed at baseline and each visit.

Eye tracking will be completed using a Tobii T120 hands free eye tracker. Subjects will view videos of social interaction positioned next to video of moving geometric objects, as well as pictures of emotional faces lasting a total of no more than 7 minutes. Eye tracking will be completed at baseline and at each visit before and after drug dosing. All eye tracking measurements will be attempted, but are not required for study participation.

Electroencephalography (EEG) will be used as an exploratory measure to assess the effects of ketamine treatment. EEG will be recorded with a whole dense array (dEEG) with 128 or 256 channel electrode cap (HydroCel Geodesic Sensor Net) continuous recording EEG system (Electrical Geodesics, Inc. (EGI), Eugene, Oreg., USA). The sensor net uses a mild, fragrance-free, saline-based solution to contact the scalp, requires approximately 10 minutes to position the net and does not require abrasion of the skin as the EGI amplifiers are design to tolerate normal skin impedances. EEG will be completed at the beginning and end of study Phases 1 and 2. All EEG measurements will be attempted, but are not required for study participation.

Study Evaluations

Safety monitoring provisions will include: Comprehensive metabolic panel, complete blood count with differential, urinalysis, serum pregnancy test in female participants of childbearing age, physical exam, vital signs, and EKG at screening visit. At each dosing visit, vitals will be monitored prior to receiving study drug dose and every 15 minutes for total of 60 minutes post study drug dose. Overall, subjects will remain in clinic for a minimum of 75 minutes post dose. Side effect review form will be administered at all visits after baseline visit.

Data and Safety Monitoring

Data Monitoring

Data will be collected on hard-copy forms and then verified by data entry personnel. Data personnel will be trained to search for potential errors and any questionable or illegible entries will be brought to the attention of the information source of the form and/or the Research Coordinator. All of these questionable or illegible entries will be addressed immediately. All of the hard copy research data is kept in locked file cabinets at the Cincinnati Children's Hospital Medical Center. Only the PI and members of the research team will have access to these files, ensuring the security of the hard copy records. Additionally, other procedures to ensure confidentiality will follow the regulations and policies of Cincinnati Children's Hospital Medical Center.

Data (such as lab values, vital signs, and outcome measure data) will be entered from source documents to case report forms (CRFs) by the study coordinator. The PI and/or other members of the study team will review case report forms entries for accuracy by comparison with the source documents. Research records and source documents will be maintained in a research chart and stored in the investigator's locked file cabinet, or in password-protected electronic files. Records will be kept secure, and individually identifiable information will not be included in any reports or data sets.

Each subject will be given a unique alphanumeric code and this will serve as the only connection between the hard-copy forms and the electronic REDcap database. The electronic database used to house the data will be password protected and only members of the study team will be given access to the database. This will protect the electronic data against any unauthorized persons from entering the dataset and jeopardizing the integrity of the data.

Statistical Analysis and Power Calculation

Data will be queried and exported to statistical software, in most cases SPSS or SAS, for data analysis. Despite the pilot nature of this project, as designed, this study will have 70% power to detect a difference in proportion of treatment responders between active treatment and placebo treatment of 0.5. The study will additionally have 80% power to detect an effect size of 1.2 on any continuous secondary outcome measure. The sample size is chosen based on recommendation for sampling in pilot studies where little is known about treatment response rates.[72] The primary endpoint analysis will be completed using Fisher's Exact Test to compare the number of treatment responders during drug versus placebo treatment. Fisher's Exact Test will also be used to analyze adverse effect occurrence in the two groups. Independent sample t tests will be applied for analysis of continuous variables. Adjustments for multiplicity in the statistical analysis will not be made given the pilot nature of the project. We will additionally utilize a generalized linear mixed model (specifically logistic regression) to analyze the impact of treatment order on outcome. Overall, the results of this project will inform future trial design including providing the data necessary for future large-scale study power calculation and primary outcome measure choice.

Safety Monitoring

An independent study medical monitor will be used for the study. The PI and Co-investigators will be primarily responsible for monitoring data quality and adverse events. Interim analysis on a quarterly basis will focus on monitoring accrual and drop-out rates. The monitor will review recruitment and adverse events every 6 months and report assessment to PI. The independent monitor will review SAEs and significant unanticipated events as they occur.

Adverse Event Definitions and Classifications

An adverse event for the purpose of this protocol is the appearance or worsening of any undesirable sign, symptom, or medical condition occurring after starting the study drug even if the event is not considered to be related to the study drug. Medical conditions/diseases present before starting study drug (but after signing informed consent) are only considered adverse events if they worsen after starting the study drug. Abnormal laboratory values or test results constitute adverse events only if they induce clinical signs or symptoms, are considered clinically significant, or require therapy.

The occurrence of adverse events will be sought by non-directive questioning of the subject. Adverse events also may be detected when they are volunteered by the subject during or between visits or through physical examination, laboratory test, or other assessments.

As far as possible, each adverse event should be evaluated to determine:

1. Severity-mild, moderate, severe, life threatening, death or grade 1-5

2. Attribution to the study drug(s)-definite, probable, possible, unlikely, unrelated 3. Duration-start and end dates or if continuing at final assessment 4. Whether it constitutes a serious adverse event (SAE)

5. Action taken

Severity Descriptors

Adverse events will be graded as follows:

| Severity | Numerical Value | Description |
|---|---|---|
| Mild | 1 | Aware of sign, symptom, or event, but easily tolerated; does not interfere with daily routine |
| Moderate | 2 | Discomfort enough to interfere with daily routine and may require some therapeutic intervention |
| Severe | 3 | Incapacitating, significantly affects clinical status; requires therapeutic intervention |
| Life Threatening | 4 | Life-Threatening; immediate intervention required |
| Death | 5 | Adverse event causes death. |

Attribution Definitions

The investigator is responsible for adverse event attribution to determine the relatedness of the event to study drug or study procedures. Attribution will be determined as follows:

| | |
|---|---|
| Unrelated | The event is unrelated. |
| Unlikely | The event is unlikely to be related |
| Possibly Related | The event or severity of event is not usually associated, but there is no strong evidence to link the event. |
| Probably Related | The event or severity of event is such that it can likely be correlated. |
| Definitely Related | There is a strong correlation with the event. |

Expected Adverse Events

Expected adverse events are those that are a known symptom or associated condition related to ketamine or study procedures.

Unexpected Adverse Events

Unexpected adverse events are defined as any adverse event whose nature, the frequency, or severity is inconsistent with the underlying disease, disorder or condition of the subject or is not identified in the Informed Consent, or Protocol.

Serious Adverse Events

Serious adverse events (SAEs) are ones that:

Result in Death

Are life-threatening (an event in which the subject was at risk of death at the time of the event; it does not refer to an event which hypothetically might have caused death if it were more severe)

Require inpatient hospitalization (more than 24 hours) or prolongation of existing hospitalization. This does not include overnight study visits for study related procedures. Elective planned hospitalizations, unrelated to either the disease being studied or the study (e.g., for tonsillectomy), will not be considered serious adverse events.

Result in a persistent or significant disability/incapacity greater than that which existed at baseline Result in a congenital anomaly/birth defect Are, in the opinion of the investigator, an important medical event Study staff will follow adverse events until resolved, if possible. The duration of the event will be recorded (start and end dates or if continuing at final assessment). Any action taken to address the event will also be recorded.

Adverse Event Reporting

Expedited Reporting

SAEs require expedited reporting when meeting the following criteria:

Serious

Unexpected

At least possibly related to the study agent or other protocol specific activity SAEs meeting the above criteria are required to be reported to the FDA as follows:

If characterized as fatal or life-threatening, within 7 calendar days of the sponsor's initial receipt of the information If non-fatal or non-life threatening, within 15 calendar days.

The Medical Monitor will review SAEs within 48 hours after initial receipt of the information by the investigator(s) to review the PIs assignment of SAE as related or unrelated to treatment; to confirm the grading of toxicity, and assure that the study may continue.

SAEs requiring expedited reporting will be reported to the IRB concurrently.

Significant unplanned deviations from the protocol will also be reported as stipulated above.

All other serious adverse events and non-serious adverse events will be reported at the time of submission of annual reports. Likewise, minor deviations will be reported in annual reporting.

Study Monitoring Plan

Monitoring will be performed by an independent study monitoring team (trained staff from the Cincinnati Children's Hospital Medical Center clinical trials office) to ensure the study is conducted, documented, and reported in accordance with the IRB approved protocol, the International Conference on Harmonization (ICH) Good Clinical Practice (GCP) Guidelines, and applicable FDA regulatory requirements.

Targeted monitoring will occur at least annually, with the schedule for monitoring to be determined by rate of enrollment, the overall risk level of the study, identified site-level risks, and issues that may arise during the course of the study.

Monitoring will include source data verification and source data review as specified in the Monitoring Plan. The study monitor may require access to the subject medical records and other source documents needed to verify the entries on the CRF/cCRFs. The study monitor will perform verification and/or review of critical site processes as indicated, including:

Eligibility of enrolled research participants

Protocol adherence and appropriate Sponsor/IRB reporting of any protocol deviations Safety information and safety reporting Consent process and documentation Drug accountability, storage and reconciliation Record keeping of essential documents Completeness and accuracy of data entry and data query resolution Investigator oversight.

Human Subjects

A total of 24 persons age 12 to 30 years with autism spectrum disorder will participate in the ketamine treatment trial.

There are no restrictions on gender, ethnicity or social background. Females, children and members of minority groups and their subpopulations in this research will be included as available.

Informed Consent

All female subjects of childbearing potential will have a serum pregnancy test and excluded from the study if this is positive. For every subject, including subjects ≥18 years of age, their parent(s)/legal guardian(s) will be required to give voluntary written informed consent for participation. For individual ≥18 years of age and cognitively able to provide informed consent, consent will additionally be obtained. Since about 3 in 4 persons with autism spectrum disorder have intellectual disability, it is anticipated that a majority of subjects will not have the cognitive ability and understanding to give their consent or assent to participate in the project.

In addition to participation of the individual with autism spectrum disorder, each individual (including those ≥18 years of age) will need a parent or guardian to agree to participate in the protocol. The parent/guardian will serve as the informant for many of the behavioral outcome measures employed in the protocol. Parent/caregiver reported outcome measures are standard practice in autism clinical trials.

Assent is obtained from the subject (when possible) and formal written consent is obtained from the parent(s)/legal guardian(s) on the consent form approved by the Cincinnati Children's Hospital Medical Center Institutional Review Board by a member of the study team. The nature of the project, the risks, the benefits, and the alternatives to participation in the project are discussed with the subject (when possible) and the subject's parent or legal guardian. All potential subjects and their legal guardians will be encouraged to ask questions about any aspect of the study that is unclear. All questions will be answered and uncertainties clarified. All legal guardians will be provided with copies of the consent form for future reference. Appropriate clinical evaluation and treatment of the referring problem will be offered regardless of the subject's/legal guardian's decisions regarding participation in the study.

Recruitment of Subjects

Recruitment of subjects will be conducted via IRB approved electronic and paper ads distributed to individuals with autism spectrum disorder, their families, treating clinicians and agencies throughout the referral base of CCHMC and those within our existing clinical services, residential facilities, schools and group homes for the developmentally disabled. Subjects will also be recruited via flyers, brochures, other newsletters, speaking engagements made by members of the research team, and other available advertising including websites, social media, newspaper, radio and television advertisements (only once such ads are individually IRB approved).

Many subjects will be recruited from the clinical patient population base at Cincinnati Children's Hospital Medical Center. Members of the research team may also contact other healthcare providers to provide information about this research study. Additionally, an electronic medical record review preparatory to research may be conducted by members of the study team to identify potentially eligible patients from the clinic. Potentially eligible subjects' parents/legal guardian may be contacted by a member of the study team to assess interest in participation via phone or IRB approved letter. Interested subjects' parents/legal guardian will undergo a non-invasive pre-screen in which the study purpose, procedures and the inclusion/exclusion criteria will be explained. If it appears that the subject would satisfy the criteria for the study and there is still an interest in participating, subjects and their legal guardians will be scheduled for a consent and screening visit.

Risk/Benefit Assessment

Ketamine Treatment

Ketamine is an FDA-approved anesthetic agent used since the 1970s via intravenous (IV) or intramuscular (IM) administration for rapid induction of dissociative anesthesia. At IV doses of 1.0 to 1.5 mg/kg or intramuscular IM doses of 3 to 4 mg/kg, ketamine rapidly exerts its dissociative effects by "disconnecting" the thalamocortical and limbic systems, resulting in dissociation of the central nervous system from external stimuli[73]. This results in potent analgesia, sedation, and amnesia while maintaining cardiovascular stability and preserving spontaneous respiration and respiratory reflexes. Because of its safety profile, ketamine has been commonly used in painful emergency department procedures in children over the last two decades[74]. Additionally ketamine has been demonstrated to be a safe and effective option for sedation in mentally handicapped adults undergoing painful medical procedures[75]. Although ketamine is not labeled by the FDA as an analgesic, it has also long been used at doses below those required for anesthesia via a variety of delivery systems including IV, IM, oral, and intranasal (IN) for treatment of neuropathic pain, post-operative pain, breakthrough pain, and traumatic pain[76]. Lower doses of ketamine are generally well tolerated with minimal negative impact on cardiovascular or respiratory function[76]. Recently low dose ketamine has been investigated for the treatment of major depression and bipolar depression in adults via IV administration, and bipolar disorder in children via IN administration[13, 77-79]. IV doses of 0.5 mg/kg rapidly improve depression symptoms, while being relatively well tolerated with transient increase in dissociative symptoms resolving in less than 90 minutes[80]. IN administration of ketamine doses ranging from 30-120 mg per dose in 12 youth ages 6 to 19 years in open-label study resulted in improved symptoms of bipolar disorder and was well tolerated with the primarily adverse effect reported as dissociative symptoms lasting less than 60-minutes after dosing[13].

Ketamine is considered a safe anesthetic agent. Ketamine does not exert its dissociative effect via a dose-response continuum, and once dissociation is reached it does not deepen with additional ketamine administration. Therefore, unlike opiate and other anesthetic agents, increased administration does not increase the risk of respiratory depression and intubation is rarely needed[74]. A 2009 meta-analysis of 8,282 pediatric ketamine sedation cases reported a 3.9% incidence of airway or respiratory complications[81]. Respiratory depression with ketamine use is rare, and appears to be most commonly associated with rapid intravenous administration occurring at the time of peak central nervous system levels shortly after administration[74]. Ketamine is a phencyclidine derivative with potential psychomimetic action, and reports of emergence reactions including hallucination and agitation following ketamine administration for anesthesia have tempered the use of this medication at some institutions. Meta-analysis of ketamine use in children revealed a 1.4% incidence of emergence reaction[82]. The reported incidence of emergence reactions in adults varies widely, but remains relatively low ranging between 0% and 30%[74]. Prescribing information for ketamine hydrochloride reports a 12% incidence of emergence reactions ranging from pleasant dream-like states to hallucinations and delirium resolving within a few hours without residual psychological effects. A cases series in 17 mentally handicapped adults undergoing sedation for medical procedures reported no incidents of emergence reaction[75]. Generally emergence reactions with ketamine are considered to be relatively infrequent, mild, and typically resolve quickly.

Furthermore, ketamine usage at anesthetic dosages has a wide margin of safety with several documented instances of unintentional administration of overdoses in children ranging from 5 to 100 times the intended dose followed by prolonged but complete recovery[83].

Long-term repeated dosing of ketamine has not been studied in detail, as anesthetic doses are generally given sparingly, and low dose depression treatment studies have been generally time limited. Ketamine does have the potential for abuse, and has been abused recreationally although it is not known to be physically addictive. In animals prolonged ketamine exposure at high doses can result in neuronal injury[84]. In humans, ketamine abusers have been show to exhibit white mater changes, cortical grey matter deficits, and changes in cortical connectivity[84]. Additionally, concern has been raised regarding the development of biliary dilation and lower urinary tract symptoms including cystitis with chronic high dose ketamine abuse[85, 86].

Other known side effects of ketamine include nausea, vomiting, fatigue, and headache, while unpleasant are not of significant safety concern. Adverse effects specific to IN administration include transient bitter taste and burning sensation in the throat.

Intranasal dosage equivalents used in this study will be below those required for IV indication of dissociative anesthesia. In a study of ketamine plasma concentrations in children via IN administration, children ages 2-9 years weighing 10-30 kg received 3 mg/kg IN resulting in mean peak plasma concentration of 496 ng/ml (0.496 μg/ml)[87]. Generally accepted plasma levels required for ketamine induced anesthesia are 0.6-2.0 μg/ml in adults and 0.8-4.0 μg/ml in children. In this project the youngest child weighing 40 kg will never receive more than a 2 mg/kg IN dose, and thus it is anticipated that no subject will reach anesthetic plasma levels. No respiratory depression with treatment is anticipated. However, patients will be continually monitored for a minimum of 75 minutes post dose. Additionally, vital signs will be obtained every 15 minutes for total of 60 minutes post dose.

Venipuncture Procedures

The risks of venipuncture are modest and include mild discomfort, infection, bleeding, and fainting. Standard methods and precautions will be used to protect the puncture site from bleeding and infection. The Research Coordinator will be familiar with the subjects and will accompany the subject and their parents to the blood drawing setting. Parents are encouraged to remain with the subject at all times. To minimize the subject's anxiety and phobic reactions, we utilize Child Life personnel when needed and available. It will also be suggested that the parents reassure the subject concerning their safety. At the discretion of the nurse or the investigator, to help reduce pain at the site of the venipuncture, the use of a topical anesthetic cream will be offered.

Procedures for Protecting Against and Minimizing Risk

Effective screening will be used to eliminate subjects who are at greatest risk because of concurrent medical conditions. The subjects will be evaluated and cared for in an advanced well-staffed pediatric neuropsychiatric research environment. Thus, the direct observation by nursing staff and research psychiatrists will allow for careful monitoring of potential adverse effects including drug side effects. If adverse reactions become excessive, the subject will be treated and removed from the study. Psychiatric hospitalization will be facilitated by the PI and Co-I for any subject whose symptoms become difficult to manage or dangerous (hospitalization expenses covered by subject's family/their insurance provider). There will be repeated monitoring of behavior and vital signs that will allow the treatment team to assess the status of the subject and alter or terminate the study if this is warranted.

Potential Benefits

The potential benefits to subjects entering this project are several, including: subjects will receive an extensive psychiatric medical/neurological evaluation, which is provided free-of-charge; 24 individuals with autism will receive a very carefully controlled drug treatment trial with ketamine that may be effective for improving social impairment.

Risk/Benefit Ratio

The subjects will be exposed to the risks of blood sampling and the potential side effects of ketamine. For the patients, the benefits offsetting this will be a more intensive and thorough psychiatric and medical evaluation, a documented objective treatment trial, and the possibility of more accurate prescription of treatment designed to meet the individual subject's needs. Since some of the subjects will have had previous drug trials with poor response or intolerable or dangerous side effects, the opportunity for a more thorough evaluation and clinical trial would be beneficial. Thus, with the risk of drug treatment minimized, the more intensive evaluation and treatment would more than compensate for the negative risks. The overall benefit to family members and society is considerable.

Subject Cost and Payment

Subjects will receive $10 per visit for participation in this study. Other than cost of travel to and from visits and potential time away from work for caregivers, we anticipate no other costs for subjects associated with study participation.

Example 8. Study Protocol 2, Open Label Study

To address the significant need for effective treatment of core symptoms of ASD, an open label pilot study of intranasal (IN) ketamine in 12 individuals with ASD ages 12-30 years using a novel quantitative outcome measure of social impairment will be used. Additionally, to develop a ketamine-focused personalized medicine approach in ASD, incorporation of pharmacokinetic (PK) and molecular pharmacodynamic (PD) assessments into initial systematic study are proposed by addressing the Specific Aims as set forth in Example 7.

Research Design and Methods—Inclusion Criteria are the same as in Example 7.

Research Design and Methods—Exclusion Criteria are the same as in Example 7.

Figure 7:
FIG. 7 depicts a schematic of the study design of Example 8.

Study Design—the Study Design is that as shown in FIG. 7

Study Drug Dosing

Study drug will be administered at research visits, and subjects will remain on site for minimum of 75 minutes post study drug dose. Subjects will not take study drug home with them at any point in the study. All visits will occur at least 4 days apart, with maximum of 10 days between visits (goal 7 days).

Ketamine will be compounded into a mucosal atomization device which delivers 10 mg of atomized ketamine per 0.1 cc spray. Participants will self-administer (or administer with the help of a caregiver) 2 sprays (20 mg) at visit 1, 4 sprays (40 mg) at visit 2, 6 sprays (60 mg) at visit 3, 8 sprays (80 mg) at visit 4, and 8 sprays (80 mg) at visit 5, unless subject reaches treatment response (see primary outcome measure below) or experiences significant adverse effect prior to reaching 8 sprays. In case of treatment response, dose will remain constant at minimally effective/tolerated dose throughout remainder of study. In case of adverse event determined by Primary Investigator to have negative potential impact on the patient's health or safety (see safety information below for discussion of potential adverse effects), dose will be decreased to previous tolerable dose for remainder of study or study participation will be terminated depending on the severity and medical relatedness of the adverse effect.

In event of concerning medical or psychiatric adverse events between scheduled weekly visits, subjects may be seen to assess for severity of adverse event and ensure safety. During these unscheduled visits physical exam, safety labs as clinically indicated, and psychiatric review of symptoms will be completed Primary and Secondary Outcome Measures—Same as in Example 7.

Study Evaluations

Safety monitoring provisions will include: Comprehensive metabolic panel, complete blood count with differential, urinalysis, serum pregnancy test in female participants of childbearing age, physical exam, vital signs, and EKG at screening visit. At each dosing visit, vitals will be monitored prior to receiving study drug dose and every 15 minutes for total of 60 minutes post study drug dose. Overall, subjects will remain in clinic for a minimum of 75 minutes post dose. An adverse events monitoring form based on the Common Terminology Criteria for Adverse Events (CTCAE) will be administered at all visits after baseline visit.

Eye tracking will be completed using a Tobii T120 hands free eye tracker. Subjects will view videos of social interaction positioned next to video of moving geometric objects, as well as pictures of emotional faces lasting a total of no more than 7 minutes. Eye tracking will be completed at baseline and at each visit before and after drug dosing. All eye tracking measurements will be attempted, but are not required for study participation.

Electroencephalography (EEG) will be used as an exploratory measure to assess the effects of ketamine treatment. EEG will be recorded with a multi-channel, wireless portable EEG system (Emotiv EEG systems, San Francisco, Calif.). The Emotiv EEG Neuroheadset connects wirelessly to computers, and its 14 EEG channel names are based on the International 10-20 locations. The 14 channels plus 2 references offer optimization of accurate spatial resolution. EEG will be completed at the beginning and end of study. All EEG measurements will be attempted, but are not required for study participation.

ERK activation biomarker assays will be drawn at screening visit, post-dose week 1, and pre- and post-dose week 5. Assays will be analyzed in Dr. Craig Erickson's Molecular Translational Biomarker Lab at Cincinnati Children's Hospital Medical Center (CCHMC). For the ERK activation assay, about 5 mL of whole blood is layered onto 3 mL Histopaque in a 15 mL centrifuge tube, and centrifuged for 35 min at 400 g. The lymphocyte-containing cell layer is removed and transferred to RPMI-1640 for washing. After a second wash in RPMI-1640, cells are resuspended at 106 per ml and rested for 30 min. They are then stimulated by addition of phorbol myristate acetate (PMA, final conc. 40 nM) and sample aliquots are removed at short intervals, fixed (2% paraformaldehyde, 10 min.) and permeabilized (cold methanol, 30 min.) Fixed, permeabilized cells are stained by addition of Alexafluor488-labeled monoclonal antibody to phospho-ERK in the dark for 30 min. Washed, resuspended cells are analyzed in a Coulter flow cytometer; the increase in brightness, resulting from increasing amounts of phosphorylated ERK, is mapped on a curve and a value for time to half-maximum phosphorylation is obtained for each blood sample.

Levels of total sAPP (total), sAPPα, Aβ40, and Aβ42 will be analyzed from plasma specimens of subjects drawn at screening visit, post-dose week 1, and pre- and post-dose week 5. Test plasma samples will be prepared soon after collection. Briefly, plasma will be isolated from freshly drawn blood by centrifuging at 1000×g for 12 minutes. The isolated plasma samples will be further centrifuged at 10,000×g for 10 minutes for complete removal of platelets. Prepared plasma samples will be aliquoted in several microfuge tubes and stored at −80° C. to avoid repeat freeze-thaw. The test samples will be thawed on ice just before use. If necessary, the plasma samples will be diluted appropriately with the EIA buffer, and assay will be performed in duplicate measurements for the test samples and standards. Test samples in neutral pH range will be used, and steps will be taken to avoid the contamination with of organic solvents. Regarding the standard to quantify the sAPPα levels, a series of sAPPα standards in EIA buffer by serial dilutions, from 0.78 ng/mL to 50 ng/mL will be prepared. To determine sAPP levels, we will thaw the test samples at a low temperature and mixed them completely. Regarding the standard to quantify levels of sAPP, we will prepare a series of sAPP standards in EIA buffer by serial dilutions, from 0.39 ng/mL to 25 ng/mL. The ELISA plate will be pre-coated with anti-human APP (R12A1) mouse IgG (IBL). ELISA of plasma samples will be carried out as per manufacturer's protocol and similar to the method described above. This ELISA kit uses HRP-labeled anti-Human APP (R101A4) mouse IgG as the detection antibody. Levels of Aβ peptides will be assayed in platelet free plasma samples by an ultra sensitive and specific ELISA (Wako Chemical Industries, Japan). Plasma samples will be diluted 2-10 times to avoid nonspecific signals. The ELISAs use highly specific capture antibodies BA27 and BC05 to detect Aβ (1-40) and Aβ (1-42), respectively. The overall assay procedures will be performed as per the guidelines of the manufacturer. ELISA of the plasma samples will be performed in a 'blinded' manner. Most of the procedure has recently been reported by Applicant[36] and the procedures at CCHMC mirror Applicant's work initially completed at Indiana University.

Pharmacokinetic evaluation blood samples drawn to evaluate ketamine and its metabolite nor-ketamine concentrations at 30 minutes and 180 min post-dose week 1, and at 30, 90, and 240 minutes post-dose week 5. Ketamine and norketamine concentrations will be determined at a low volume, validated liquid chromatography tandem mass spectrometry (LC-MS/MS) assay in the Mass-Spec lab directed by Alexander Vinks and Ken Setchell at CCHMC. Concentration data will be analyzed by compartmental and noncompartmental pharmacokinetic analysis with the software package WinNonlin (Version 4.0.1, Pharsight Corporation, Palo Alto, Calif.) using a weighed least-squares algorithm. Population PK analysis will be conducted using NONMEM version 7.2.0 (ICON, Ellicott City, Md.) on a 64-bit Linux Operation System with an Intel Fortran Compiler (v 12.0). PDx-Pop (version 5, ICON, Ellicott City, Md.) will be used as the graphical user interface for running NONMEM and for processing NONMEM output. Visualization of NONMEM output was implemented by Xpose 4 package in R (v 2.15.0.). First order conditional estimation with interaction (FOCE-I) will be employed throughout to simultaneously estimate the typical population PK parameters, random effect of inter-individual variability and residual errors. Model structure selection will be based on goodness-of-fit criteria, including convergence with at least 3 significant digits, diagnostic plots, physiological plausibility of the parameter estimates and Akaike Information Criterion (AIC). Inter-individual variability (IIV) will be modeled using an exponential model which assumes a normally distributed inter-individual variable with a mean of zero and a variance of ω2. Parameter estimates generated will include Cmax, total body clearance, distribution and elimination half-lives, volume of distribution and the area under the curve (AUC).

Data and Safety Monitoring

Data Monitoring—Same as in Example 7.

Statistical Analysis

As this project matures into the data analysis stage, data will be queried and exported to statistical software, in most cases SPSS or SAS, for data analysis. Our sample size was chosen based on recommendation for sampling in pilot studies where little is known about treatment response rates[72]. Our sample size will allow us to estimate effect size which will guide development of future placebo controlled study. Paired sample t-tests will be utilized in the analysis of continuous variables. Fisher's Exact test will be employed in the analysis of categorical variables. Data will be summarized with means and standard deviations reported. We will not make adjustments for multiplicity in the statistical analysis given the pilot nature of the project. We will additionally utilize a generalized linear mixed model (specifically logistic regression) to analyze the impact of treatment order on outcome. Overall, the results of this project will inform future trial design including providing the data necessary for future large-scale study power calculation and primary outcome measure choice.

Correlation analysis between ERK activation, plasma APP derivatives, clinical response, adverse events and PK AUC will be modeled using regression analysis in SPSS. Comparison of plasma levels of sAPP-total, sAPPα, Aβ40, Aβ42, as well as the ratios of sAPPα/sAPP and Aβ42/Aβ40 pre- and post-ketamine treatment will be primary outcomes analzed for the APP biomarker. For the ERK activation marker, primary outcomes will include baseline lymphocytic p-ERK levels and time to half maximum ERK phosphorylation following lymphocyte activation. All blood biomarker data will be coded into IBM SPSS Statistics 21 or SAS 9.4 for analysis. The differences between pre- and post-assay values for APP and ERK will be compared by paired t-tests in the patient sample, by bootstrap resampling of the mean difference in the individual treatment groups and 95% confidence intervals and Hedge's g calculated. An exploratory Kendall's tau correlation analysis will be conducted to assess for any relationship between change in primary APP and/or ERK activation outcomes above and change in behavioral outcome measures that may show change during the course of the clinical trial.

Safety Monitoring—Same as in Example 7.

Adverse Event Definitions and Classifications—Same as in Example 7.

Adverse Event Reporting—Same as in Example 7.

Expedited Reporting—Same as in Example 7.

Study Monitoring Plan—Same as in Example 7.

Human Subjects

A total of 12 persons age 12 to 30 years with autism spectrum disorder will participate in the ketamine treatment trial.

There are no restrictions on gender, ethnicity or social background. We plan to include when available females, children and members of minority groups and their subpopulations in this research.

Informed Consent—Same as in Example 7.

Recruitment of Subject—Same as in Example 7.

Venipuncture Procedures—Same as in Example 7

Procedures for Protecting Against and Minimizing Risk—Same as in Example 7

Potential Benefits—Same as in Example 7

Risk/Benefit Ratio—Same as in Example 7

Subject Cost and Payment—Same as in Example 7

REFERENCES

1. Prevention CfDCa. Autism Spectrum Disorder, Data and Statistics. 2014; http://www.cdc.gov/ncbddd/autism/data.html
2. American PA. *Diagnostic and Statistical Manual of Mental Disorders, Fifth Edition*. Arlington, Va.: American Psychiatric Association; 2013.
3. Wink L K, Erickson C A, McDougle C J. Pharmacologic treatment of behavioral symptoms associated with autism and other pervasive developmental disorders. *Curr Treat Options Neurol*. November 2010; 12(6):529-538.
4. Erickson C A, McDougle C J, Stigler K A, Posey D J. Glutamatergic function in autism. In: Heresco-Levy U, ed. *Glutamate in Neuropsychiatric Disorders*. Trivandrum, Kerala, India: Research Signpost; 2008.
5. King B H, Wright D M, Handen B L, et al. Double-blind, placebo-controlled study of amantadine hydrochloride in the treatment of children with autistic disorder. *J Am Acad Child Adolesc Psychiatry*. June 2001; 40(6):658-665.
6. Posey D, Stigler K, Erickson C A, et al. A double-blind, placebo-controlled study of D-Cycloserine in children with autistic disorder. Paper presented at: 2008 Annual Meeting of the American Academy of Child and Adolescent Psychiatry 2008; Chicago, Ill.
7. Erickson C A, Mullett J E, McDougle C J. Open-Label Memantine in Fragile X Syndrome. *J Autism Dev Disord*. Jul. 16, 2009.
8. Erickson C A, Posey D J, Stigler K A, Mullett J, Katschke A R, McDougle C J. A retrospective study of memantine in children and adolescents with pervasive developmental disorders. *Psychopharmacology*. March 2007; 191 (1): 141-147.
9. Seeman P, Caruso C, Lasaga M. Memantine agonist action at dopamine D2High receptors. *Synapse*. February 2008; 62(2):149-153.
10. Orser B A, Pennefather P S, MacDonald J F. Multiple mechanisms of ketamine blockade of N-methyl-D-aspartate receptors. *Anesthesiology*. April 1997; 86(4):903-917.
11. Kavalali E T, Chung C, Khvotchev M, et al. Spontaneous neurotransmission: an independent pathway for neuronal signaling? *Physiology (Bethesda)*. February 2011; 26(1): 45-53.
12. Aan Het Rot M, Zarate C A, Jr., Charney D S, Mathew S J. Ketamine for depression: where do we go from here? *Biol Psychiatry*. Oct. 1, 2012; 72(7):537-547.
13. Papolos D F, Teicher M H, Faedda G L, Murphy P, Mattis S. Clinical experience using intranasal ketamine in the treatment of pediatric bipolar disorder/fear of harm phenotype. *J Affect Disord*. May 2013; 147(1-3):431-436.

14. Shaffer R, Wink L K, Gaietto K, Bowers K, Erickson C A. Novel Social Preference Eye Tracking Task in Autism Spectrum Disorder. *Journal of Autism and Developmental Disorders*. 2013.
15. The_interagency_Autism_Coordinating_Committee. 2011 Strategic Plan for Autism Spectrum Disorder Research. *NIH Publication No.* 10-7573: Department of Health & Human Services USA; 2011.
16. Hurko O, Walsh F S. Novel drug development for amyotrophic lateral sclerosis. *J Neurol Sci*. Nov. 1, 2000; 180(1-2):21-28.
17. Uenishi H, Huang C S, Song J H, Marszalec W, Narahashi T. Ion channel modulation as the basis for neuroprotective action of MS-153. *Ann NY Acad Sci*. 1999; 890:385-399.
18. Bushell T, Clarke C, Mathie A, Robertson B. Pharmacological characterization of a non-inactivating outward current observed in mouse cerebellar Purkinje neurones. *Br J Pharmacol*. February 2002; 135(3):705-712.
19. Niebroj-Dobosz I, Janik P, Kwiecinski H. Effect of Riluzole on serum amino acids in patients with amyotrophic lateral sclerosis. *Acta Neurol Scand*. July 2002; 106(1):39-43.
20. He Y, Benz A, Fu T, et al. Neuroprotective agent riluzole potentiates postsynaptic GABA(A) receptor function. *Neuropharmacology*. February 2002; 42(2):199-209.
21. Westphalen R I, Hemmings H C, Jr. Selective depression by general anesthetics of glutamate versus GABA release from isolated cortical nerve terminals. *J Pharmacol Exp Ther*. March 2003; 304(3):1188-1196.
22. Cook E H, Jr. Genetics of autism. *Child Adolesc Psychiatr Clin N Am*. April 2001; 10(2):333-350.
23. Bailey D B, Jr., Hatton D D, Skinner M, Mesibov G. Autistic behavior, FMR1 protein, and developmental trajectories in young males with fragile X syndrome. *J Autism Dev Disord*. April 2001; 31(2):165-174.
24. Hatton D D, Sideris J, Skinner M, et al. Autistic behavior in children with fragile X syndrome: prevalence, stability, and the impact of FMRP. *Am J Med Genet A*. Sep. 1, 2006; 140A(17):1804-1813.
25. Kim S H, Markham J A, Weiler I J, Greenough W T. Aberrant early-phase ERK inactivation impedes neuronal function in fragile X syndrome. *Proc Natl Acad Sci USA*. Mar. 18, 2008; 105(11):4429-4434.
26. Weng N, Weiler I J, Sumis A, Berry-Kravis E, Greenough W T. Early-phase ERK activation as a biomarker for metabolic status in fragile X syndrome. *Am J Med Genet B Neuropsychiatr Genet*. Oct. 5, 2008; 147B(7): 1253-1257.
27. Levitt P, Campbell D B. The genetic and neurobiologic compass points toward common signaling dysfunctions in autism spectrum disorders. *J Clin Invest*. April 2009; 119(4):747-754.
28. Aylward E H, Minshew N J, Field K, Sparks BF, Singh N. Effects of age on brain volume and head circumference in autism. *Neurology*. Jul. 23, 2002; 59(2):175-183.
29. Davidovitch M, Patterson B, Gartside P. Head circumference measurements in children with autism. *J Child Neurol*. September 1996; 11(5):389-393.
30. McCaffery P, Deutsch C K. Macrocephaly and the control of brain growth in autistic disorders. *Prog Neurobiol*. September-October 2005; 77(1-2):38-56.
31. Courchesne E, Carper R, Akshoomoff N. Evidence of brain overgrowth in the first year of life in autism. *JAMA*. Jul. 16, 2003; 290(3):337-344.
32. Courchesne E, Karns C M, Davis H R, et al. Unusual brain growth patterns in early life in patients with autistic disorder: an MRI study. *Neurology*. Jul. 24, 2001; 57(2):245-254.
33. Courchesne E, Pierce K. Brain overgrowth in autism during a critical time in development: implications for frontal pyramidal neuron and interneuron development and connectivity. *Int J Dev Neurosci*. April-May 2005; 23(2-3):153-170.
34. Sparks B F, Friedman S D, Shaw D W, et al. Brain structural abnormalities in young children with autism spectrum disorder. *Neurology*. Jul. 23, 2002; 59(2):184-192.
35. Hazlett H C, Poe M D, Gerig G, et al. Early brain overgrowth in autism associated with an increase in cortical surface area before age 2 years. *Arch Gen Psychiatry*. May 2011; 68(5):467-476.
36. Lahiri D K, Sokol D K, Erickson C, Ray B, Ho C Y, Maloney B. Autism as early neurodevelopmental disorder: evidence for an sAPPalpha-mediated anabolic pathway. *Frontiers in cellular neuroscience*. 2013; 7:94.
37. Ray B, Long J M, Sokol D K, Lahiri D K. Increased secreted amyloid precursor protein-alpha (sAPPalpha) in severe autism: proposal of a specific, anabolic pathway and putative biomarker. *PLoS ONE*. 2011; 6(6):e20405.
38. Sokol D K, Chen D, Farlow M R, et al. High levels of Alzheimer beta-amyloid precursor protein (APP) in children with severely autistic behavior and aggression. *J Child Neurol*. June 2006; 21(6):444-449.
39. Sokol D K, Maloney B, Long J M, Ray B, Lahiri D K. Autism, Alzheimer disease, and fragile X: APP, FMRP, and mGluR5 are molecular links. *Neurology*. Apr. 12, 2011; 76(15):1344-1352.
40. Lahiri D K, Farlow M R, Sambamurti K, Greig N H, Giacobini E, Schneider L S. A critical analysis of new molecular targets and strategies for drug developments in Alzheimer's disease. *Current drug targets*. February 2003; 4(2): 97-112.
41. Mattson M P, Furukawa K. Signaling events regulating the neurodevelopmental triad. Glutamate and secreted forms of beta-amyloid precursor protein as examples. *Perspectives on developmental neurobiology*. 1998; 5(4): 337-352.
42. Mullan M, Crawford F. Genetic and molecular advances in Alzheimer's disease. *Trends Neurosci*. October 1993; 16(10):398-403.
43. Jolly-Tornetta C, Gao Z Y, Lee V M, Wolf B A. Regulation of amyloid precursor protein secretion by glutamate receptors in human Ntera 2 neurons. *J Biol Chem*. May 29, 1998; 273(22):14015-14021.
44. Priller C, Bauer T, Mitteregger G, Krebs B, Kretzschmar H A, Herms J. Synapse formation and function is modulated by the amyloid precursor protein. *J Neurosci*. Jul. 5, 2006; 26(27):7212-7221.
45. Lahiri D K, Nall C, Chen D, Zaphiriou M, Morgan C, Nurnberger J I, Sr. Developmental expression of the beta-amyloid precursor protein and heat-shock protein 70 in the cerebral hemisphere region of the rat brain. *Ann NY Acad Sci*. June 2002; 965:324-333.
46. Mattson M P. Secreted forms of beta-amyloid precursor protein modulate dendrite outgrowth and calcium responses to glutamate in cultured embryonic hippocampal neurons. *J Neurobiol*. April 1994; 25(4):439-450.
47. Schubert D, Jin L W, Saitoh T, Cole G. The regulation of amyloid beta protein precursor secretion and its modulatory role in cell adhesion. *Neuron*. December 1989; 3(6):689-694.

48. Young-Pearse T L, Bai J, Chang R, Zheng J B, LoTurco J J, Selkoe D J. A critical function for beta-amyloid precursor protein in neuronal migration revealed by in utero RNA interference. *J Neurosci*. Dec. 26, 2007; 27(52):14459-14469.
49. Mattson M P. Cellular actions of beta-amyloid precursor protein and its soluble and fibrillogenic derivatives. *Physiological reviews*. October 1997; 77(4):1081-1132.
50. Stein T D, Johnson J A. Genetic programming by the proteolytic fragments of the amyloid precursor protein: somewhere between confusion and clarity. *Reviews in the neurosciences*. 2003; 14(4):317-341.
51. Turner P R, O'Connor K, Tate W P, Abraham W C. Roles of amyloid precursor protein and its fragments in regulating neural activity, plasticity and memory. *Prog Neurobiol*. May 2003; 70(1):1-32.
52. Barger S W, Harmon A D. Microglial activation by Alzheimer amyloid precursor protein and modulation by apolipoprotein E. *Nature*. Aug. 28, 1997; 388(6645):878-881.
53. Greig N H, Utsuki T, Ingram D K, et al. Selective butyrylcholinesterase inhibition elevates brain acetylcholine, augments learning and lowers Alzheimer beta-amyloid peptide in rodent. *Proc Natl Acad Sci USA*. Nov. 22, 2005; 102(47):17213-17218.
54. Lahiri D K, Lewis S, Farlow M R. Tacrine alters the secretion of the beta-amyloid precursor protein in cell lines. *J Neurosci Res*. Apr. 15, 1994; 37(6):777-787.
55. Lahiri D K, Farlow M R, Sambamurti K. The secretion of amyloid beta-peptides is inhibited in the tacrine-treated human neuroblastoma cells. *Brain Res Mol Brain Res*. Nov. 20, 1998; 62(2): 131-140.
56. Bailey A R, Giunta B N, Obregon D, et al. Peripheral biomarkers in Autism: secreted amyloid precursor protein-alpha as a probable key player in early diagnosis. *International journal of clinical and experimental medicine*. 2008; 1(4):338-344.
57. McFarlane H G, Kusek G K, Yang M, Phoenix J L, Bolivar V J, Crawley J N. Autism-like behavioral phenotypes in BTBR T+tf/J mice. *Genes Brain Behav*. March 2008; 7(2):152-163.
58. Moy S S, Nadler J J, Young N B, et al. Mouse behavioral tasks relevant to autism: phenotypes of 10 inbred strains. *Behav Brain Res*. Jan. 10, 2007; 176(1):4-20.
59. Yang M, Zhodzishsky V, Crawley J N. Social deficits in BTBR T+tf/J mice are unchanged by cross-fostering with C57BL/6J mothers. *Int J Dev Neurosci*. December 2007; 25(8):515-521.
60. Chadman K K. Fluoxetine but not risperidone increases sociability in the BTBR mouse model of autism. *Pharmacol Biochem Behav*. January 2011; 97(3):586-594.
61. Silverman J L, Oliver C F, Karras M N, Gastrell P T, Crawley J N. AMPAKINE enhancement of social interaction in the BTBR mouse model of autism. *Neuropharmacology*. January 2013; 64:268-282.
62. Silverman J L, Tolu S S, Barkan C L, Crawley J N. Repetitive self-grooming behavior in the BTBR mouse model of autism is blocked by the mGluR5 antagonist MPEP. *Neuropsychopharmacology*. March 2010; 35(4): 976-989.
63. Mayer S, Harris B, Gibson D A, et al. Acamprosate has no effect on NMDA-induced toxicity but reduces toxicity induced by spermidine or by changing the medium in organotypic hippocampal slice cultures from rat. *Alcohol Clin Exp Res*. May 2002; 26(5):655-662.
64. Naassila M, Hammoumi S, Legrand E, Durbin P, Daoust M. Mechanism of action of acamprosate. Part I. Characterization of spermidine-sensitive acamprosate binding site in rat brain. *Alcohol Clin Exp Res*. June 1998; 22(4):802-809.
65. Palucha-Poniewiera A, Pile A. Involvement of mGlu5 and NMDA receptors in the antidepressant-like effect of acamprosate in the tail suspension test. *Prog Neuropsychopharmacol Biol Psychiatry*. Oct. 1, 2012; 39(1):102-106.
66. Fumagalli E, Funicello M, Rauen T, Gobbi M, Mennini T. Riluzole enhances the activity of glutamate transporters GLAST, GLT1 and EAAC1. *Eur J Pharmacol*. Jan. 14, 2008; 578(2-3):171-176.
67. Doble A. The pharmacology and mechanism of action of riluzole. *Neurology*. December 1996; 47(6 Suppl 4):S233-241.
68. Wang S J, Wang K Y, Wang W C. Mechanisms underlying the riluzole inhibition of glutamate release from rat cerebral cortex nerve terminals (synaptosomes). *Neuroscience*. 2004; 125(1):191-201.
69. Erickson C A, Weng N, Weiler I J, et al. Open-label riluzole in fragile X syndrome. *Brain Res*. Mar. 22, 2011; 1380:264-270.
70. Erickson C, Schaefer T L, Wink L K, et al. Acamprosate on Amyloid Precursor Protein in Youth with Idiopathic and Fragile X Syndrome-Associated Autism Spectrum Disorder. Paper presented at: American Academy of Child and Adolescent Psychiatry Annual Meeting 2013; Orlando, Fla.
71. Kalk N, Lingford-Hughes A. The Clinical Pharmacology of Acamprosate. *Br J Clin Pharmacol*. 2012.
72. Julious S. Sample size of 12 per group rue of thumb for a pilot study. *Pharmaceutical Statistics*. 2005; 4:287-291.
73. Green S M, Krauss B. Clinical practice guideline for emergency department ketamine dissociative sedation in children. *Ann Emerg Med*. November 2004; 44(5):460-471.
74. Green S M, Roback M G, Kennedy R M, Krauss B. Clinical practice guideline for emergency department ketamine dissociative sedation: 2011 update. *Ann Emerg Med*. May 2011; 57(5):449-461.
75. Green S M, Rothrock S G, Hestdalen R, Ho M, Lynch E L. Ketamine sedation in mentally disabled adults. *Academic emergency medicine: official journal of the Society for Academic Emergency Medicine*. January 1999; 6(1):86-87.
76. Carr D B, Goudas L C, Denman W T, et al. Safety and efficacy of intranasal ketamine for the treatment of breakthrough pain in patients with chronic pain: a randomized, double-blind, placebo-controlled, crossover study. *Pain*. March 2004; 108(1-2):17-27.
77. Zarate C A, Jr., Singh J B, Carlson P J, et al. A randomized trial of an N-methyl-D-aspartate antagonist in treatment-resistant major depression. *Arch Gen Psychiatry*. August 2006; 63(8):856-864.
78. Zarate C A, Jr., Brutsche N E, Ibrahim L, et al. Replication of ketamine's antidepressant efficacy in bipolar depression: a randomized controlled add-on trial. *Biol Psychiatry*. Jun. 1, 2012; 71(11):939-946.
79. Berman R M, Cappiello A, Anand A, et al. Antidepressant effects of ketamine in depressed patients. *Biol Psychiatry*. Feb. 15, 2000; 47(4):351-354.
80. Ibrahim L, Diazgranados N, Luckenbaugh D A, et al. Rapid decrease in depressive symptoms with an N-methyl-d-aspartate antagonist in ECT-resistant major depression. *Prog Neuropsychopharmacol Biol Psychiatry*. Jun. 1, 2011; 35(4):1155-1159.

81. Green S M, Roback M G, Krauss B, et al. Predictors of airway and respiratory adverse events with ketamine sedation in the emergency department: an individual-patient data meta-analysis of 8,282 children. *Ann Emerg Med*. August 2009; 54(2):158-168 el51-154.
82. Green S M, Roback M G, Krauss B, et al. Predictors of emesis and recovery agitation with emergency department ketamine sedation: an individual-patient data meta-analysis of 8,282 children. *Ann Emerg Med*. August 2009; 54(2):171-180 e171-174.
83. Green S M, Clark R, Hostetler M A, Cohen M, Carlson D, Rothrock S G. Inadvertent ketamine overdose in children: clinical manifestations and outcome. *Ann Emerg Med*. October 1999; 34(4 Pt 1):492-497.
84. Krystal J H, Sanacora G, Duman R S. Rapid-acting glutamatergic antidepressants: the path to ketamine and beyond. *Biol Psychiatry*. Jun. 15, 2013; 73(12):1133-1141.
85. Chen L Y, Chen K P, Huang M C. Cystitis associated with chronic ketamine abuse. *Psychiatry Clin Neurosci*. August 2009; 63(4):591.
86. Wong S W, Lee K F, Wong J, Ng W W, Cheung Y S, Lai P B. Dilated common bile ducts mimicking choledochal cysts in ketamine abusers. *Hong Kong Med J*. February 2009; 15(1):53-56.
87. Malinovsky J M, Servin F, Cozian A, Lepage J Y, Pinaud M. Ketamine and norketamine plasma concentrations after i.v., nasal and rectal administration in children. *Br J Anaesth*. August 1996; 77(2):203-207.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating an autism spectrum disorder in a subject in need thereof, comprising the step of intranasally administering a composition comprising ketamine and a pharmaceutically acceptable excipient and/or carrier to said subject in need thereof, wherein said administration step comprises administering a dose of ketamine of from about 20 to about 120 mg ketamine.

2. The method according to claim 1, wherein said composition comprises racemic ketamine.

3. The method according to claim 1, wherein said composition comprises S-ketamine.

4. The method according to claim 1, wherein said composition comprises greater than about 50% of the S enantiomer of ketamine.

5. The method according to claim 1, wherein said composition is substantially free of R-ketamine.

6. The method according to claim 1, wherein said composition further comprises an agent for treating autism selected from atypical antipsychotics, stimulants, serotonin reuptake inhibitors, alpha 2 agonists, and a combination thereof.

7. The method according to claim 1, wherein said composition is administered weekly.

8. The method according to claim 1, wherein said composition is administered daily.

9. The method according to claim 1, wherein said composition is administered in an escalating dose.

10. The method according to claim 1, wherein said composition further comprises an agent selected from a permeation enhancer, a polymer capable of increasing mucosal adhesion of the composition, or a combination thereof.

11. A method of treating an autism spectrum disorder in a subject in need thereof, comprising the step of intranasally administering a composition comprising ketamine and a pharmaceutically acceptable excipient and/or carrier to said subject in need thereof, wherein said administration step comprises intranasal administration, wherein said treatment comprises administering intranasal ketamine in an amount sufficient to improve social engagement in said subject, wherein said administration step comprises administering a dose of ketamine of from about 20 to about 120 mg ketamine.

12. The method according to claim 11 wherein said composition is substantially free of R-ketamine.

13. A method of improving social engagement in a subject diagnosed with ASD, comprising administering ketamine intranasally, wherein said ketamine is administered at a dose of from about 20 to about 120 mg to said subject.

14. The method according to claim 1, wherein said composition is administered every two to seven days.

* * * * *